(12) United States Patent
Wrasidlo et al.

(10) Patent No.: US 11,078,196 B2
(45) Date of Patent: *Aug. 3, 2021

(54) HETEROARYL AMIDES AS INHIBITORS OF PROTEIN AGGREGATION

(71) Applicant: UCB Biopharma SRL, Brussels (BE)

(72) Inventors: Wolfgang Wrasidlo, La Jolla, CA (US); Emily M. Stocking, Encinitas, CA (US)

(73) Assignee: UCB Biophama SRL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/438,348

(22) Filed: Jun. 11, 2019

(65) Prior Publication Data
US 2019/0308965 A1 Oct. 10, 2019

Related U.S. Application Data

(63) Continuation of application No. 15/666,503, filed on Aug. 1, 2017, now Pat. No. 10,358,443, which is a continuation of application No. 14/983,243, filed on Dec. 29, 2015, now Pat. No. 9,738,635, which is a continuation of application No. PCT/US2015/013263, filed on Jan. 28, 2015.

(60) Provisional application No. 62/078,895, filed on Nov. 12, 2014, provisional application No. 61/933,246, filed on Jan. 29, 2014.

(51) Int. Cl.
| | | |
|---|---|---|
| C07D 417/12 | (2006.01) | |
| C07D 417/14 | (2006.01) | |
| C07D 403/12 | (2006.01) | |
| C07D 413/12 | (2006.01) | |

(52) U.S. Cl.
CPC ......... *C07D 417/12* (2013.01); *C07D 403/12* (2013.01); *C07D 413/12* (2013.01); *C07D 417/14* (2013.01)

(58) Field of Classification Search
CPC .. C07D 417/12; C07D 403/12; C07D 413/12; C07D 417/14
See application file for complete search history.

(56) References Cited

U.S. PATENT DOCUMENTS

| | | |
|---|---|---|
| 8,846,682 B2 | 9/2014 | Masliah et al. |
| 9,284,309 B2 | 3/2016 | Wrasidlo |
| 2013/0274260 A1 | 10/2013 | Griffioen et al. |
| 2015/0183776 A1 | 7/2015 | Wrasidlo |
| 2016/0207912 A1 | 7/2016 | Wrasidlo |
| 2019/0367502 A1 | 12/2019 | Hall |
| 2019/0367513 A1 | 12/2019 | Hall |

FOREIGN PATENT DOCUMENTS

| | | |
|---|---|---|
| WO | WO2010/142801 A1 | 12/2010 |
| WO | WO2011/084642 A1 | 7/2011 |
| WO | WO2013/134371 A1 | 9/2013 |
| WO | WO2013/148365 A1 | 10/2013 |
| WO | WO2014/014937 A1 | 1/2014 |
| WO | WO-2015/116663 | 8/2015 |
| WO | WO-2017/020010 A1 | 2/2017 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995) (Year: 1995).*
Awad, R.A. "Neurogenic Bowel Dysfunction in Patients with Spinal Cord Injury, Myelomeningocele, Multiple Sclerosis, and Parkinson's Disease," *World J. Gastroenterol.* 2011, 17(46), 5035-5048.
Bagshawe, K.D., "Antibody-Directed Enzyme Prodrug Therapy: A Review," *Drug Dev. Res.* 1995, 34, 220-230.
Berge, S.M. et al., "Pharmaceutical Salts," *J. Pharm. Sci.* 1977, 66, 1-19.
Bertolini, G. et al., "A New Rational Hypothesis for the Pharmacophore of the Active Metabolite of Leflunomide, a Potent Immunosuppressive Drug," *J. Med. Chem.* 1997, 40, 2011-2016.
Bodis-Wollner, I. et al., "Fovea and Foveation in Parkinson's Disease," *Behav. Neurosci.* 2013, 127(2), 139-150.
Bodis-Wollner, I., "Foveal Vision Is Impaired in Parkinson's Disease," *Parkinsonism Relat. Disord.* 2013, 19(1), 1-14.
Bodis-Wollner, I. et al., "α-Synuclein in the Inner Retina in Parkinson Disease," *Ann. Neurol.* 2014, 75(6), 964-6.
Bodner, C.R. et al., "Differential Phospholipid Binding of α-Synuclein Variants Implicated in Parkinson's Disease Revealed by Solution NMR Spectroscopy," *Biochemistry* 2010, 49, 862-871.
Bodor, N., "Novel Approaches to the Design of Safer Drugs: Soft Drugs and Site-Specific Chemical Delivery Systems," *Adv. Drug Res.* 1984, 13, 255-331.
Botha, H. and J. Carr, "Attention and Visual Dysfunction in Parkinson's Disease," *Parkinsonism Relat. Disord.* 2012, 18(6), 742-747.
Brooks, D.J., "Positron Emission Tomography and Single-Photon Emission Computed Tomography in Central Nervous System Drug Development," *NeuroRx* 2005, 2(2), 226-236.
Cannon, J.G. in: Burger's Medicinal Chemistry and Drug Discovery, Fifth Edition, vol. 1: Principles and Practice, Wiley-Interscience (1995) Ch. 19, pp. 783-802.
Delaglio, F. et al., "NMRPipe: A Multidimensional Spectral Processing System Based in UNIX Pipes," *J. Biomol. NMR* 1995, 6, 277-293.

(Continued)

*Primary Examiner* — Marcos L Sznaidman
(74) *Attorney, Agent, or Firm* — Morrison & Foerster LLP

(57) ABSTRACT

The present invention relates to certain heteroaryl amide compounds, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, Parkinson's disease with dementia, frontotemporal dementia, Huntington's Disease, amyotrophic lateral sclerosis, and multiple system atrophy, and cancer and melanoma.

37 Claims, 12 Drawing Sheets

Specification includes a Sequence Listing.

(56) References Cited

OTHER PUBLICATIONS

Fleming, S.M., "Cardiovascular Autonomic Dysfunction in Animal Models of Parkinson's Disease," *J. Parkinsons Dis.* 2011, 1(4), 321-327.
International Preliminary Report on Patentability for PCT/US2015/013263, dated Jan. 7, 2016, 18 pages.
International Search Report and Written Opinion for International Application No. PCT/US2015/013263, dated Apr. 23, 2015, 9 pages.
Jain, S. and D.S. Goldstein, "Cardiovascular Dysautonomia in Parkinson Disease: From Pathophysiology to Pathogenesis," *Neurobiol. Dis.* 2012, 46(3), 572-580.
Javaid, M.A. et al., "Cortical Control of Voluntary Saccades in Parkinson's Disease and Pre-emptive Perception," *Parkinsonism Relat. Disord.* 2012, 18(Suppl. 1), S100-3.
Jellinger, K.A., "Synuclein Deposition and Non-motor Symptoms in Parkinson Disease," *J. Neurol. Sci.* 2011, 310(1-2), 107-111.
Kaufmann, H. and D.S. Goldstein, "Chapter 21—Autonomic Dysfunction in Parkinson Disease," *Handbook Clin. Neurol.* 2013, 117, 259-278.
Kim, J.S. et al., "Anorectal Dysfunctions in Parkinson's Disease," *J. Neurol. Sci.* 2011, 310(1-2), 144-151.
Loudon, G.M., Organic Chemistry, 4$^{th}$ Edition, New York: Oxford University Press, 2002, pp. 360-361, 1084-1085.
Masliah E. et al., "Dopaminergic Loss and Inclusion Body Formation in α-Synuclein Mice: Implications for Neurodegenerative Disorders," *Science* 2000, 287(5456):1265-9.
Pan, T. et al., "The Role of Alpha-Synuclein in Melanin Synthesis in Melanoma and Dopaminergic Neuronal Cells," PLoS One 2012, 7(9), e45183.
Post, K.K. et al., "Cardiac Denervation and Dysautonomia in Parkinson's Disease: A Review of Screening Techniques," *Parkinsonism Relat. Disord.* 2008, 14(7), 524-531.
Rao, J. N. et al., "Effect of Pseudorepeat Rearrangement on α-Synuclein Misfolding, Vesicle Binding, and Micelle Binding," *J. Mol. Biol.* 2009, 390, 516-529.
Rockenstein, E. et al., "Retinal Scanning Evaluations of Alpha-Synuclein-eGFP Deposition in a Transgenic Mouse Model of PD/DLB," Society for Neurosciences, Annual Meeting, Nov. 11, 2013, Abstract No. 329.06.
Rockenstein, E. et al., "Lysosomal Pathology Associated with a-Synuclein Accumulation in Transgenic Models Using an eGFP Fusion Protein," *J. Neurosci. Res.* 2005, 80, 247-259.
Schanda, P. et al., "SOFAST-HMQC Experiments for Recording Two-Dimensional Deteronuclear Correlation Spectra of Proteins within a Few Seconds," *J. Biomol. NMR* 2005, 33, 199-211.
Senard, J.M. and A. Pathak, "Neurogenic Orthostatic Hypotension of Parkinson's Diseas: What Exploration for What Treatment?" *Rev. Neurol. (Paris)* 2010, 166(10), 779-784.
Shan, D. et al., "Prodrug Strategies Based on Intramolecular Cyclization Reactions," *J. Pharm. Sci.* 1997, 86 (7), 765-767.
Wang, L. et al. "Mice Overexpressing Wild-Type Human Alpha-Synuclein Display Alterations in Colonic Myenteric Ganglia and Defecation," *Neurogastroenterol. Motil.* 2012, 24(9), e425-436.
Yu, J.G. et al., "Retinal Nerve Fiber Layer Thickness Changes in Parkinson Disease: A Meta-Analysis," *PLoS One* 2014, 9(1), e85718.
International Search Report and Written Opinion for PCT/US16/44871, dated Oct. 18, 2016, 8 pages.
International Search Report and Written Opinion for PCT/EP2018/051579, dated May 16, 2018, 9 pages.
International Search Report and Written Opinion for PCT/EP2018/051580, dated Mar. 12, 2018, 13 pages.
International Search Report and Written Opinion for PCT/EP2018/051584, dated Mar. 21, 2018, 12 pages.
Non-Final Office Action for U.S. Appl. No. 15/666,503, dated Jul. 27, 2018, 7 pages.
Pubchem: "MolPort-010-919-232 | $C_{21}H_{29}N_5O_3S$—Pubchem," Jun. 21, 2011, 9 pages, retrieved from the Internet: URL:http://pubchem.ncbi.nlm.nih.gov/compound/53161072#section=Chemical-Vendors [retrieved on Mar. 14, 2017].
Pubchem: "MolPort-010-919-196 | $C_{21}H_{29}N_5O_3S$—PubChem," Jun. 21, 2011, 9 pages, retrieved from the Internet: URL:http://pubchem.ncbi.nlm.nih.gov/compound/53161036#section=Top [retrieved on Mar. 14, 2017].
Pubchem: "MolPort-010-919-163 | $C_{20}H_{27}N_5O_2S$—PubChem," Jun. 21, 2011, 9 pages, retrieved from the Internet: URL:http://pubchem.ncbi.nlm.nih.gov/compound/53161003#section=Top [retrieved on Mar. 14, 2017].
Pubchem: "MolPort-028-860-176 | $C_{20}H_{26}FN_5O_2S$—PubChem," Nov. 29, 2013, 9 pages, retrieved from the Internet: URL:http://pubchem.ncbi.nlm.nih.gov/compound/71840278#section=Substrances-by-Category [retrieved on Mar. 14, 2017].
Pubchem: "MolPort-028-860-061 | $C_{20}H_{26}FN_5OS$—PubChem," Nov. 29, 2013, 9 pages, retrieved from the Internet: URL:http://pubchem.ncbi.nlm.nih.gov/compound/71840292#section=Information-Sources [retrieved on Mar. 14, 2017].
Pubchem: "MolPort-028-860-051 | $C_{22}H_{31}N_5O_2S$—PubChem," Nov. 29, 2013, 9 pages, retrieved from the Internet: URL:http://pubchem.ncbi.nlm.nih.gov/compound/71840396#section=Chemical-Vendors [retrieved on Mar. 14, 2017].
Pubchem: "SR-01000649247 | $C_{19}H_{26}N_6O_2S$—PubChem," Feb. 21, 2016, 9 pages, retrieved from the Internet: URL:http://pubchem.ncbi.nlm.nih.gov/compound/117082374#section=Top [retrieved on Mar. 14, 2017].
Pubchem: "SR-01000647965 | $C_{19}H_{26}N_6O_2S$—PubChem," Feb. 11, 2016, 9 pages, retrieved from the Internet: URL:http://pubchem.ncbi.nlm.nih.gov/compound/117080913#section=Top retrieved on Mar. 14, 2017.
Dermer, "Another Anniversary for the War on Cancer," Bio/Technology (1994) 12:320.
Freshney, Culture of Animal Cells, A Manual of Basic Technique, Alan R. Liss, Inc., 1983, New York, p. 4.
Layzer, "Degenerative Diseases of the Nervous System," in: Cecil Textbook of Medicine, Bennet and Plum (eds.), 20th Edition, W.B. Saunders Co. (1996) vol. 2, pp. 2050-2057.

\* cited by examiner

1A

1B

HETEROARYL AMIDES AS INHIBITORS OF PROTEIN AGGREGATION

CROSS REFERENCE TO RELATED APPLICATIONS

This application is a continuation of U.S. patent application Ser. No. 15/666,503, filed Aug. 1, 2017, which is a continuation of U.S. patent application Ser. No. 14/983,243, filed Dec. 29, 2015, now U.S. Pat. No. 9,738,635, issued Aug. 22, 2017, which is a continuation of International Application No. PCT/US2015/013263, filed Jan. 28, 2015, which claims the benefit of U.S. Provisional Applications No. 61/933,246, filed Jan. 29, 2014, and No. 62/078,895, filed Nov. 12, 2014, the contents of which are incorporated herein by reference in their entireties.

TECHNICAL FIELD

The present invention relates to certain heteroaryl amide derivatives, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, Parkinson's disease with dementia, fronto-temporal dementia, Huntington's Disease, amyotrophic lateral sclerosis, and multiple system atrophy, and cancer.

SEQUENCE LISTING

The content of the following submission on ASCII text file is incorporated herein by reference in its entirety: a computer readable form (CRF) of the Sequence Listing (file name: 794512000803SeqList.TXT; date recorded: Jun. 11, 2019; size: 755 bytes).

BACKGROUND

Neurodegenerative disorders of the aging population such as Alzheimer's disease (AD), Parkinson's disease (PD), and fronto-temporal dementia (FTD), affect over 20 million people in the United States and European Union alone and rank among the top causes of death for the elderly. A common feature among these neurological disorders is the chronic accumulation of proteins into neurotoxic aggregates. Each disease is characterized by the specific neuronal populations that are affected, the particular protein aggregates that are involved, and the clinical features that result from the neuronal degeneration.

Studies suggest that the initial stages of protein aggregation involve mutation or post-translational modification (e.g., nitrosilation, oxidation) of the target protein, which then adopts an abnormal conformation that facilitates interactions with similarly misfolded proteins. The abnormal proteins then aggregate to form dimers, trimers, and higher-order multimers, also termed "soluble oligomers," which may disrupt synaptic function. Additionally, the aggregates may then anchor in the cell membrane and form globular oligomers (which in turn can form pores in the membrane) and/or protofibrils or fibrils. These larger, insoluble fibrils may function as reservoirs of the bioactive oligomers.

Diverse lines of evidence support the notion that the progressive accumulation of protein aggregates is causally involved in the pathogenesis of neurodegenerative diseases. A number of other proteins may accumulate in the brains of patients with neurodegeneration, such as alpha-synuclein, Aβ protein, Tau, and TDP43. The cognitive impairment of these patients is closely associated with synaptic loss in the neocortex and limbic systems and increasing levels protein aggregates may contribute to this synaptic loss. Much research is focused on detailing the mechanisms through which accumulation of alpha-synuclein and other amyloid precursor proteins (APP) metabolites contributes to synaptic damage and neurodegeneration. Many studies support the hypothesis that formation of small aggregates, also known as oligomers, plays a major role in neurotoxicity. These peptide oligomers can organize into dimers, trimers, tetramers, pentamers, and other higher order arrays that can form annular structures. High levels of such oligomers are predictive of dementia and synaptic loss in patients. Because evidence indicates the oligomers rather than smaller precursor fibrils are the toxic species, compounds that target these early aggregation processes in a specific manner would be useful as potential new therapies for PD, AD and related conditions.

Various neurodegenerative diseases involve the accumulation of neurotoxic protein-based aggregates. In idiopathic Parkinson's disease (IPD), dementia with Lewy bodies (LBD), Parkinson's disease with dementia (PDD), and multiple system atrophy (MSA), the neurotoxic aggregates are composed of α-synuclein (SYN), which is a synaptic protein that is intracellular under normal conditions. In FTD and amyotrophic lateral sclerosis (ALS), neurotoxic aggregates originate from other intracellular proteins such as tau, TDP-43, or SOD1. For certain diseases, such as AD, SYN aggregates with the primary protein (e.g., Aβ protein). In Huntington's Disease, aggregates form from the cleavage products of Htt proteins.

Accumulation of α-synuclein has also been implicated in cancer, in particular, in melanoma cancer cells. Pan et al., PLoS One 2012, 7(9), e45183. Thus, compounds that inhibit such accumulation may prove useful in treatment of various cancers, including melanoma.

Two mechanisms are implicated in these protein aggregation processes. In the first, the misfolded and/or aggregated proteins anchor to the various cell membrane structures. Binding of the misfolded or aggregated molecules to the plasma membrane or the membranes of organelles (e.g., mitochondria or lysosomes) may interfere with protein transcription, autophagy, mitochondrial function, and pore formation. By way of example, neurotoxic SYN aggregates and interacts with lipids in cell membranes by a specific portion of the c-terminal region of the synuclein protein. Compounds that bind to this region can inhibit protein-protein or protein-lipid interactions and can therefore be used to block neurotoxic oligomerization of SYN or other proteins and their interactions with membranes. In the second process, aggregated protein is released from the anchored subunit and propagates to adjacent cells. This cell-to-cell propagation of toxic protein aggregates may then underlie the anatomic progression of neurodegeneration and worsening of symptoms. Small molecule drugs that interact with the target proteins may limit release and/or propagation, and therefore reduce the neurotoxic effects of aggregated proteins.

Compounds that are inhibitors of protein aggregation are described in PCT Publ. Nos. WO2011/084642, WO2013/148365, WO2013/134371, and PCT Appln. No. PCT/US2013/050719.

There remains a need for inhibitors of protein aggregation with desirable pharmaceutical properties. Certain heteroaryl amide compounds have been found in the context of this invention to have protein aggregation modulating activity.

SUMMARY OF THE INVENTION

In one aspect, the invention relates to a chemical entity of the following Formula (I):

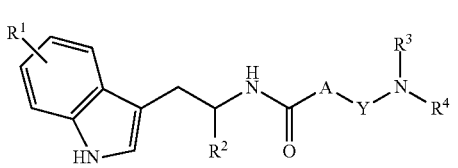

wherein
- $R^1$ is H, halo, $C_{1-4}$alkyl, or $CF_3$;
- $R^2$ is H, —$CF_3$, or $C_{1-4}$alkyl unsubstituted or substituted with halo or —$CF_3$;
- A is a 5-membered heteroaryl ring;
- Y is absent or is $C_{1-4}$alkylene;
- $R^3$ and $R^4$ taken together with the nitrogen to which they are attached form a monocyclic heterocycloalkyl ring, unsubstituted or substituted with $C_{1-4}$alkyl; or
  where Y is $C_{1-4}$alkylene, $R^3$ and Y taken together with the nitrogen to which $R^3$ is attached form a monocyclic heterocycloalkyl ring, and $R^4$ is H or $C_{1-4}$alkyl;
or a pharmaceutically acceptable salt thereof.

In certain embodiments, the compound of Formula (I) is a compound selected from those species described or exemplified in the detailed description below.

In a further aspect, the invention relates to a pharmaceutical composition comprising at least one compound of Formula (I) or a pharmaceutically acceptable salt thereof. Pharmaceutical compositions according to the invention may further comprise a pharmaceutically acceptable excipient. The invention is also a compound of Formula (I) or a pharmaceutically acceptable salt thereof for use as a medicament.

In another aspect, the invention is directed to a method of treating a neurodegenerative disease or condition associated with protein or peptide aggregation comprising administering to a subject in need of such treatment an effective amount of at least one compound of Formula (I) or a pharmaceutically acceptable salt thereof.

In another aspect, the invention is directed to a method of treating a disease or medical condition associated with protein or peptide aggregation, comprising administering to a subject in need of such treatment an effective amount of at least one compound of Formula (I) or a pharmaceutically acceptable salt thereof. The invention is also directed at use of a compound of Formula (I) in the preparation of a medicament for the treatment of such diseases and medical conditions, and the use of such compounds and salts for treatment of such diseases and medical conditions.

In yet another aspect, the invention relates to a method of interfering with the accumulation of protein or peptide aggregates in a cell, or preventing, slowing, reversing, or inhibiting protein or peptide aggregation in a cell, comprising contacting the cell with an effective amount of at least one compound of Formula (I) or a salt thereof, and/or with at least one pharmaceutical composition of the invention, wherein the contacting is in vitro, ex vivo, or in vivo.

Additional embodiments, features, and advantages of the invention will be apparent from the following detailed description and through practice of the invention.

For the sake of brevity, the disclosures of the publications cited in this specification, including patents, are herein incorporated by reference.

BRIEF DESCRIPTION OF THE FIGURES

In FIG. 1A, the Y axis (I/Io) is the ratio of the heteronuclear single quantum coherence (HSQC) spectroscopy signal intensity for ASYN (average of residues 3-23) in the presence (I) or absence (Io) of lipid membranes. In FIG. 1B, the average I/Io ratio of ASYN residues 3-23 was plotted as a function of the concentration of Example 1 added.

FIG. 6A reflects the ASYN neuropil arm, and FIG. 6B reflects the neuronal cell body arm of the study.

FIG. 7C).

DETAILED DESCRIPTION OF THE INVENTION

Figure 1:
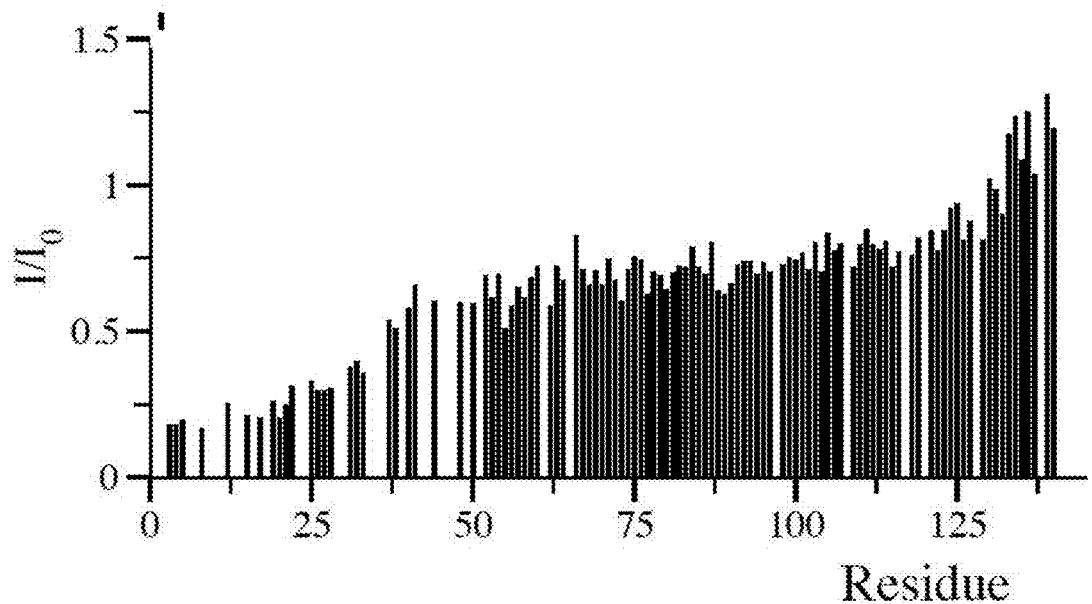
FIG. 1 shows the results of Biological Example 3.
Figure 1:
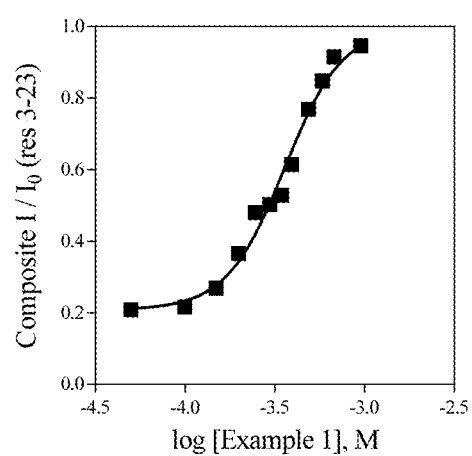
Figure 2:
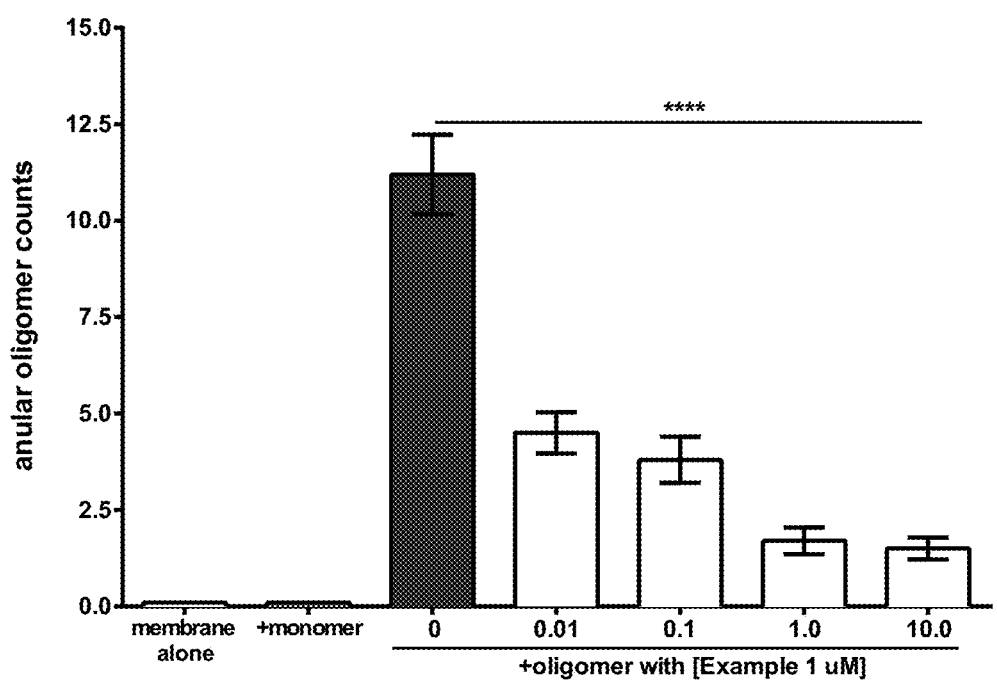
FIG. 2 shows the quantification of electron microscopic images of ASYN oligomers in the absence and presence of Example 1, as described in Biological Example 4.
Figure 3:
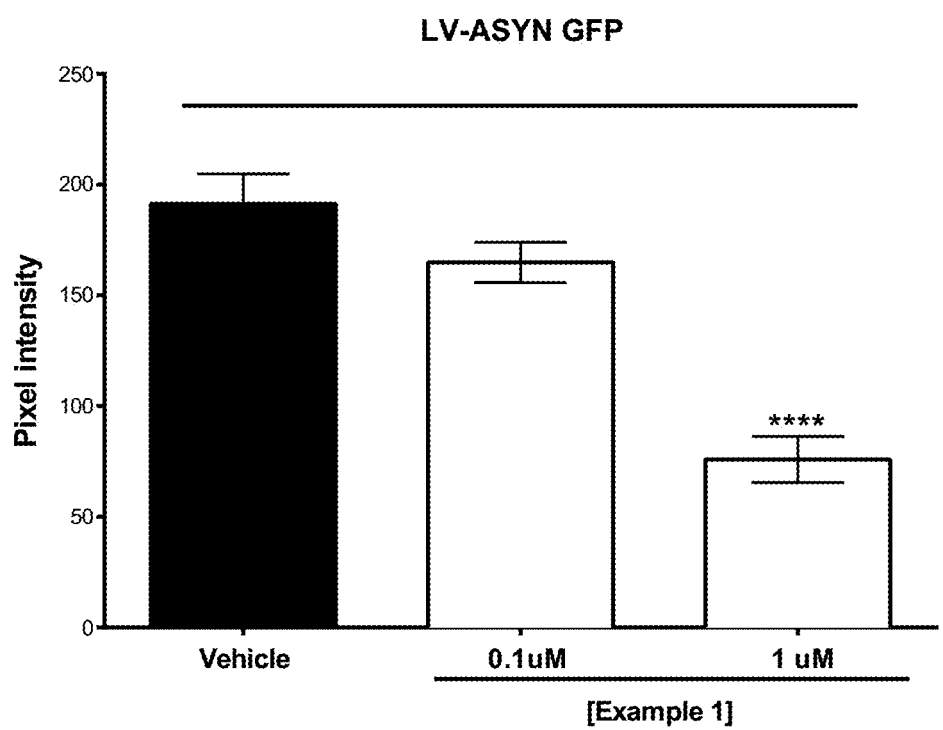
FIG. 3 shows the effect of Example 1 on the accumulation of ASYN in B103 neuroblastoma cells expressing GFP-tagged human ASYN, as described in Biological Example 5.
Figure 4:
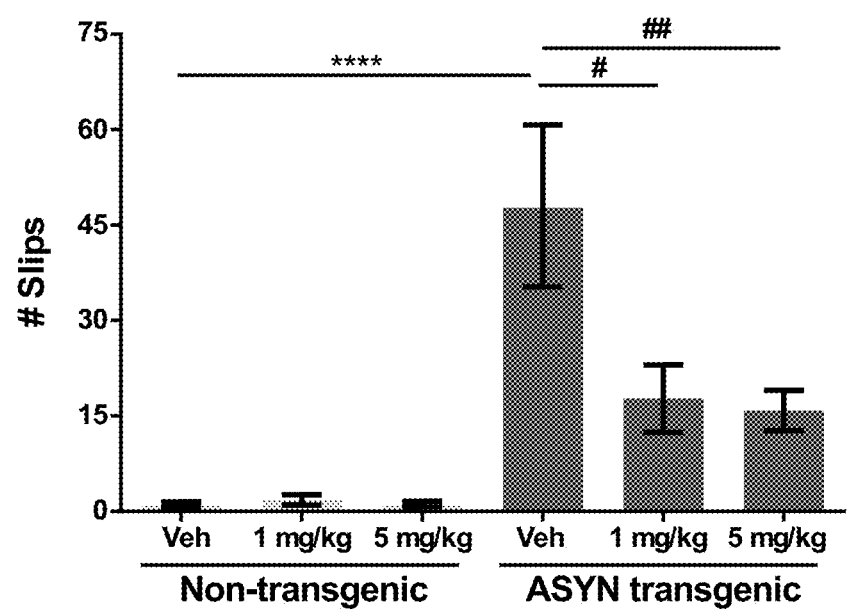
FIG. 4 shows the results of Biological Example 6A and the effects of Example 1 at 1 mg/kg and 5 mg/kg dosing on transgenic mice in the Round Beam Task model.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available AutoNom software (MDL, San Leandro, Calif.), Version 12.0.2.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Representative Embodiments

In some embodiments of Formula (I), $R^1$ is H, fluoro, chloro, bromo, methyl, ethyl, propyl, isopropyl, butyl, isobutyl, sec-butyl, or tert-butyl. In other embodiments, $R^1$ is H or fluoro. In other embodiments, $R^1$ is H. In other embodiments, $R^1$ is fluoro.

In some embodiments, $R^2$ is H, —$CF_3$, or is methyl, ethyl, propyl, isopropyl, butyl, isobutyl, sec-butyl, or tert-butyl, each unsubstituted or substituted with fluoro, chloro, bromo, or —$CF_3$. In other embodiments, $R^2$ is H. In other embodiments, $R^2$ is —$CF_3$ or is $C_{1-4}$alkyl optionally substituted with halo or —$CF_3$. In other embodiments, $R^2$ is $C_{3-4}$alkyl, unsubstituted or substituted with fluoro or —$CF_3$. In other embodiments, $R^2$ is butyl. In other embodiments, $R^2$ is propyl substituted with —$CF_3$.

In some embodiments, $R^2$ is in the "R" stereochemical configuration. In other embodiments, $R^2$ is in the "S" stereochemical configuration. In other embodiments, compounds of Formula (I) are stereochemical mixtures at the $R^2$ position. In still other embodiments, $R^2$ is substantially "R" or substantially "S" stereochemical configuration.

In some embodiments, A is a 5-membered heteroaryl ring with two or three heteroatom ring atoms. In other embodiments, A is a 5-membered heteroaryl ring with two non-adjacent heteroatom ring atoms. In still other embodiments, A is thiazole, thiadiazole, oxazole, imidazole, or triazole. In still other embodiments, A is thiazole or thiadiazole. In still other embodiments, A is thiazole.

In some embodiments, Y is absent. In other embodiments, Y is —$CH_2$—, —$CH_2CH_2$—, —$CH(CH_3)$—, —$(CH_2)_3$—, —$C(CH_3)_2$—, —$(CH_2)_4$—, —$CH((CH_2)_2CH_3)$—, —$CH(CH(CH_3)_2)$—, —$CH(CH_2CH_3)CH_2$—, —$CH(CH_3)CH(CH_3)$—, —$CH(CH_3)(CH_2)_2$—, or —$CH_2CH(CH_3)CH_2$—. In other embodiments, Y is —$CH_2$—, —$CH_2CH_2$—, or —$CH(CH_3)$—. In still other embodiments, Y is —$CH_2$—.

In some embodiments, $R^3$ and $R^4$ are taken together with the nitrogen to which they are attached form a monocyclic heterocycloalkyl ring, unsubstituted or substituted with $C_{1-4}$alkyl. In other embodiments, $R^3$ and $R^4$ taken together with the nitrogen to which they are attached form azetidine, pyrrolidine, piperidine, azepine, piperazine, morpholine, thiomorpholine, or 1,1-dioxo-thiomorpholine, each unsubstituted or substituted with $C_{1-4}$alkyl. In other embodiments, $R^3$ and $R^4$ taken together with the nitrogen to which they are attached form piperazine, morpholine, or pyrrolidine, each unsubstituted or substituted with $C_{1-4}$alkyl. In other embodiments, $R^3$ and $R^4$ taken together with the nitrogen to which they are attached form piperazine or morpholine, each unsubstituted or substituted with $C_{1-4}$alkyl. In other embodiments, $R^3$ and $R^4$ taken together with the nitrogen to which they are attached form piperazine, unsubstituted or substituted with $C_{1-4}$alkyl. In still other embodiments, $R^3$ and $R^4$ taken together with the nitrogen to which they are attached form piperazine or 4-methyl-piperazine.

In other embodiments, where Y is $C_{1-4}$alkylene, $R^3$ and Y are taken together with the nitrogen to which $R^3$ is attached form a monocyclic heterocycloalkyl ring, and $R^4$ is H or $C_{1-4}$alkyl. In other embodiments, Y and $R^3$ taken together with the nitrogen to which $R^3$ is attached form pyrrolidine or piperidine. In other embodiments, $R^4$ is H or methyl.

In some embodiments, $R^1$ is H, $R^2$ is H or $C_{1-4}$alkyl (or is H, or is $C_{3-4}$alkyl), A is thiazole, Y is absent or is ethylene (or is absent, or is ethylene), and $R^3$ and $R^4$ taken together with the nitrogen to which they are attached form N-methylpiperazine.

In other embodiments, the compound of Formula (I) is selected from the group consisting of:

| Ex. | Structure | Chemical Name |
| --- | --- | --- |
| 1 | 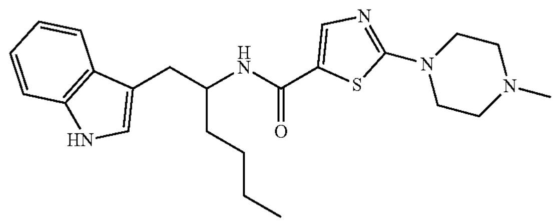 | N-(1-(1H-Indol-3-yl)hexan-2-yl)-2-(4-methylpiperazin-1-yl)thiazole-5-carboxamide |
| 2 | 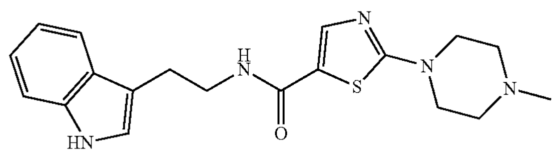 [SMILES: CN1CCN(c2ncc(C(=O)NCCc3c[nH]c4ccccc34)s2)CC1] | N-(2-(1H-Indol-3-yl)ethyl)-2-(4-methylpiperazin-1-yl)thiazole-5-carboxamide |
| 3 | 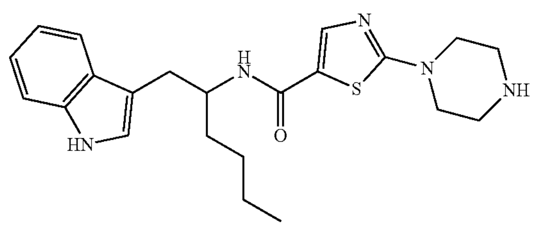 [SMILES: CCCCC(Cc1c[nH]c2ccccc12)NC(=O)c1cnc(N2CCNCC2)s1] | N-(1-(1H-Indol-3-yl)hexan-2-yl)-2-(piperazin-1-yl)thiazole-5-carboxamide |
| 4 | 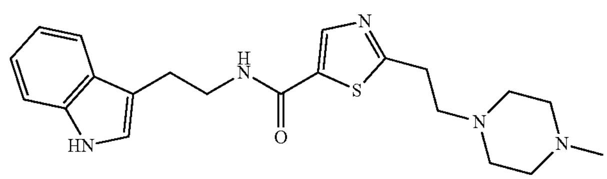 [SMILES: CN1CCN(CCc2ncc(C(=O)NCCc3c[nH]c4ccccc34)s2)CC1] | N-(2-(1H-Indol-3-yl)ethyl)-2-(2-(4-methylpiperazin-1-yl)ethyl)thiazole-5-carboxamide |
| 5 | 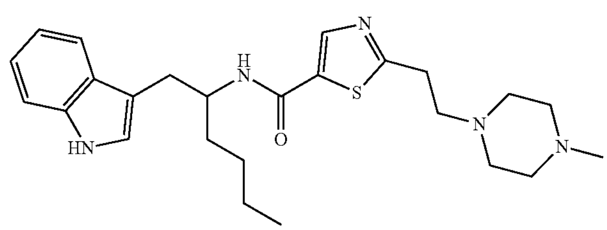 [SMILES: CCCCC(Cc1c[nH]c2ccccc12)NC(=O)c1cnc(CCN2CCN(C)CC2)s1] | N-(1-(1H-Indol-3-yl)hexan-2-yl)-2-(2-(4-methylpiperazin-1-yl)ethyl)thiazole-5-carboxamide |
| 6 | 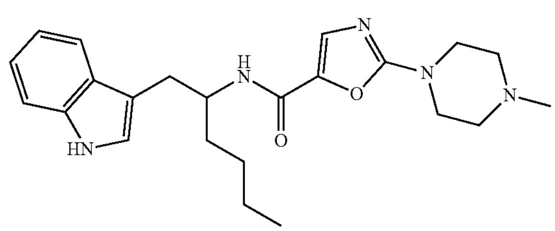 [SMILES: CCCCC(Cc1c[nH]c2ccccc12)NC(=O)c1cnc(N2CCN(C)CC2)o1] | N-(1-(1H-Indol-3-yl)hexan-2-yl)-2-(4-methylpiperazin-1-yl)oxazole-5-carboxamide |
| 7 | 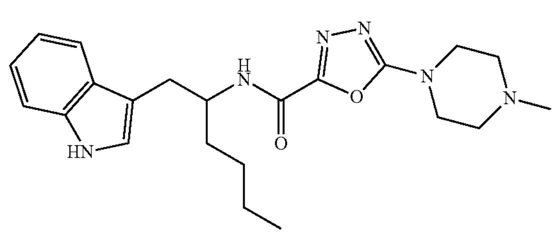 [SMILES: CCCCC(Cc1c[nH]c2ccccc12)NC(=O)c1nnc(N2CCN(C)CC2)o1] | N-(1-(1H-Indol-3-yl)hexan-2-yl)-5-(4-methylpiperazin-1-yl)-1,3,4-thiadiazole-2-carboxamide |

| Ex. | Structure | Chemical Name |
|---|---|---|
| 8 | 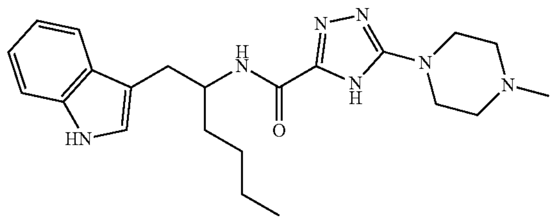 [SMILES: CCCCC(Cc1c[nH]c2ccccc12)NC(=O)c1nnc(N2CCN(C)CC2)[nH]1] | N-(1-(1H-Indol-3-yl)hexan-2-yl)-5-(4-methylpiperazin-1-yl)-4H-1,2,4-triazole-3-carboxamide |
| 9 | 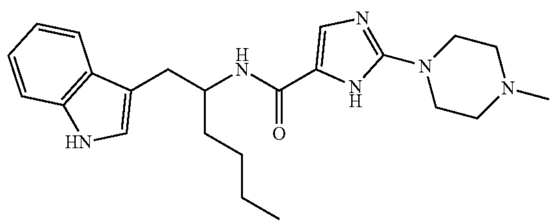 [SMILES: CCCCC(Cc1c[nH]c2ccccc12)NC(=O)c1cnc(N2CCN(C)CC2)[nH]1] | N-(1-(1H-Indol-3-yl)hexan-2-yl)-2-(4-methylpiperazin-1-yl)-1H-imidazole-5-carboxamide |
| 10 | 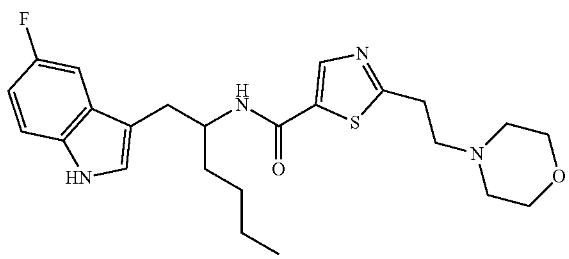 [SMILES: CCCCC(Cc1c[nH]c2ccc(F)cc12)NC(=O)c1cnc(CCN2CCOCC2)s1] | N-(1-(5-Fluoro-1H-indol-3-yl)hexan-2-yl)-2-(2-morpholinoethyl)thiazole-5-carboxamide |
| 11 | 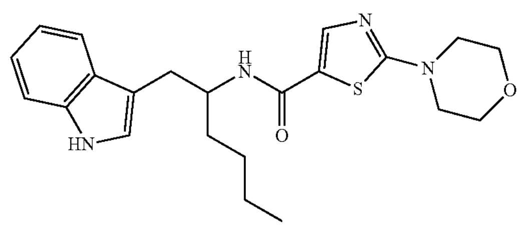 [SMILES: CCCCC(Cc1c[nH]c2ccccc12)NC(=O)c1cnc(N2CCOCC2)s1] | N-(1-(1H-Indol-3-yl)hexan-2-yl)-2-morpholinothiazole-5-carboxamide |
| 12 | 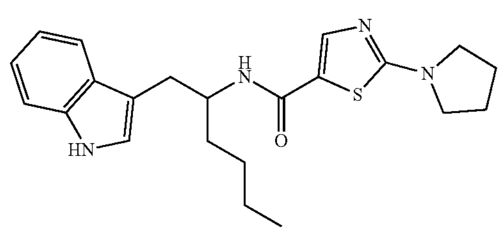 [SMILES: CCCCC(Cc1c[nH]c2ccccc12)NC(=O)c1cnc(N2CCCC2)s1] | N-(1-(1H-indol-3-yl)hexan-2-yl)-2-(pyrrolidin-1-yl)thiazole-5-carboxamide |
| 13 | 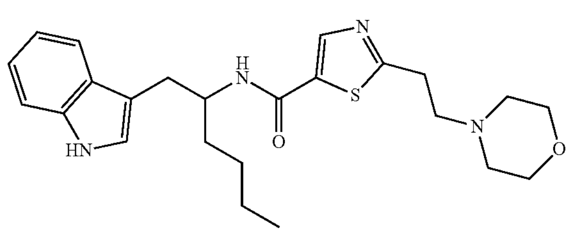 [SMILES: CCCCC(Cc1c[nH]c2ccccc12)NC(=O)c1cnc(CCN2CCOCC2)s1] | N-(1-(1H-indol-3-yl)hexan-2-yl)-2-(2-morpholinoethyl)thiazole-5-carboxamide |

| Ex. | Structure | Chemical Name |
|---|---|---|
| 14 | 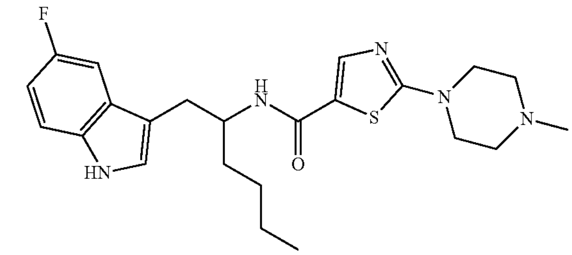 [SMILES: CCCCC(Cc1c[nH]c2ccc(F)cc12)NC(=O)c1cnc(N2CCN(C)CC2)s1] | N-(1-(5-fluoro-1H-indol-3-yl)hexan-2-yl)-2-(4-methylpiperazin-1-yl)thiazole-5-carboxamide |
| 15 | 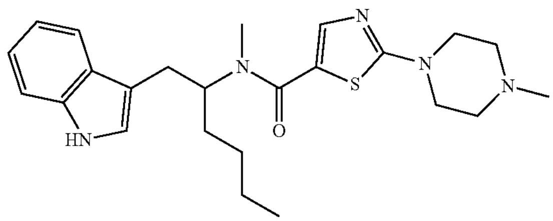 [SMILES: CCCCC(Cc1c[nH]c2ccccc12)N(C)C(=O)c1cnc(N2CCN(C)CC2)s1] | N-(1-(1H-indol-3-yl)hexan-2-yl)-N-methyl-2-(4-methylpiperazin-1-yl)thiazole-5-carboxamide |
| 16 | 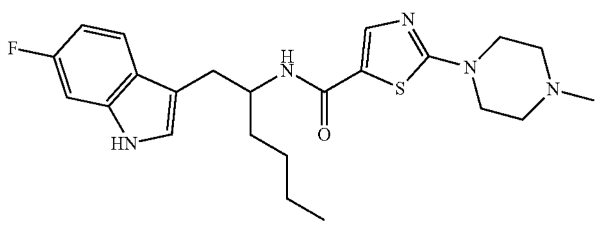 [SMILES: CCCCC(Cc1c[nH]c2cc(F)ccc12)NC(=O)c1cnc(N2CCN(C)CC2)s1] | N-(1-(6-fluoro-1H-indol-3-yl)hexan-2-yl)-2-(4-methylpiperazin-1-yl)thiazole-5-carboxamide |
| 17 | 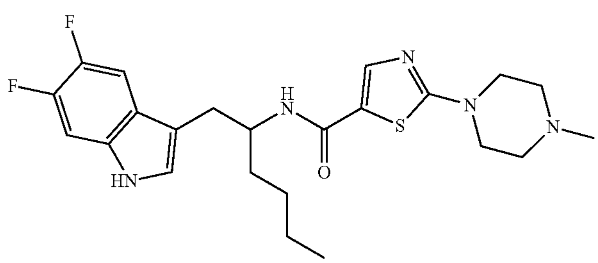 [SMILES: CCCCC(Cc1c[nH]c2cc(F)c(F)cc12)NC(=O)c1cnc(N2CCN(C)CC2)s1] | N-(1-(5,6-difluoro-1H-indol-3-yl)hexan-2-yl)-2-(4-methylpiperazin-1-yl)thiazole-5-carboxamide |
| 18 | 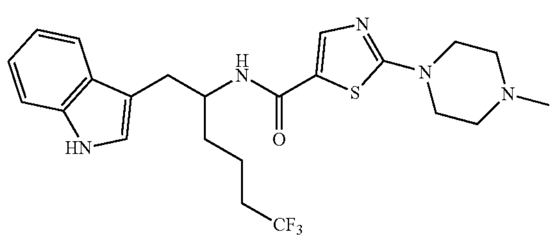 [SMILES: CN1CCN(c2ncc(C(=O)NC(CCCC(F)(F)F)Cc3c[nH]c4ccccc34)s2)CC1] | 2-(4-methylpiperazin-1-yl)-N-(6,6,6-trifluoro-1-(1H-indol-3-yl)hexan-2-yl)thiazole-5-carboxamide |
| 19 | 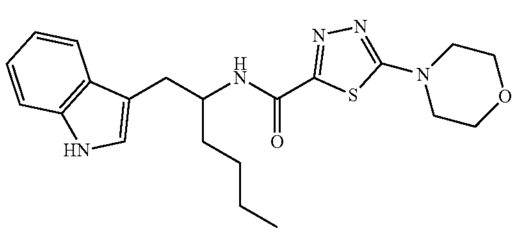 [SMILES: CCCCC(Cc1c[nH]c2ccccc12)NC(=O)c1nnc(N2CCOCC2)s1] | N-(1-(1H-indol-3-yl)hexan-2-yl)-5-morpholino-1,3,4-thiadiazole-2-carboxamide |

| Ex. | Structure | Chemical Name |
|---|---|---|
| 20 | 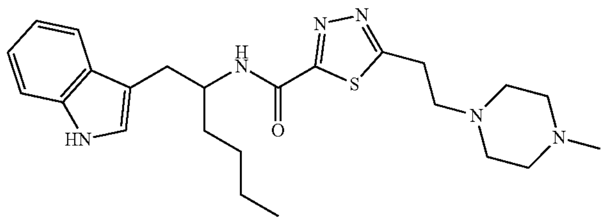 [SMILES: CCCCC(Cc1c[nH]c2ccccc12)NC(=O)c1nnc(CCN2CCN(C)CC2)s1] | N-(1-(1H-indol-3-yl)hexan-2-yl)-5-(2-(4-methylpiperazin-1-yl)ethyl)-1,3,4-thiadiazole-2-carboxamide |
| 21 | 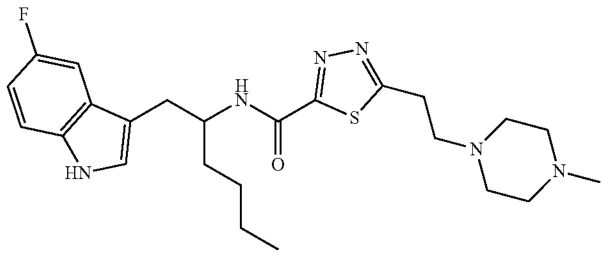 [SMILES: CCCCC(Cc1c[nH]c2ccc(F)cc12)NC(=O)c1nnc(CCN2CCN(C)CC2)s1] | N-(1-(5-fluoro-1H-indol-3-yl)hexan-2-yl)-5-(2-(4-methylpiperazin-1-yl)ethyl)-1,3,4-thiadiazole-2-carboxamide |
| 22 | 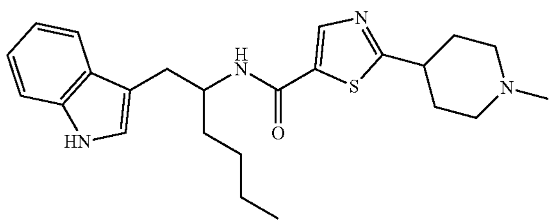 [SMILES: CCCCC(Cc1c[nH]c2ccccc12)NC(=O)c1cnc(C2CCN(C)CC2)s1] | N-(1-(1H-indol-3-yl)hexan-2-yl)-2-(1-methylpiperidin-4-yl)thiazole-5-carboxamide |
| 23 | 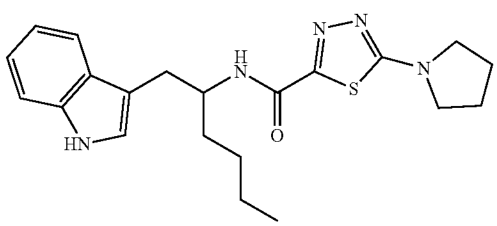 [SMILES: CCCCC(Cc1c[nH]c2ccccc12)NC(=O)c1nnc(N2CCCC2)s1] | N-(1-(1H-indol-3-yl)hexan-2-yl)-5-(pyrrolidin-1-yl)-1,3,4-thiadiazole-2-carboxamide |
| 24 | 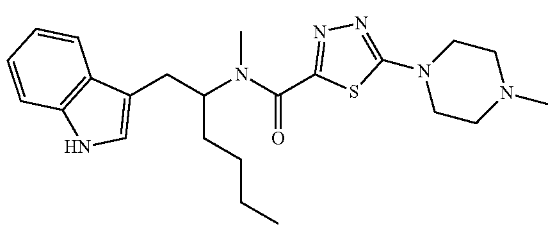 [SMILES: CCCCC(Cc1c[nH]c2ccccc12)N(C)C(=O)c1nnc(N2CCN(C)CC2)s1] | N-(1-(1H-indol-3-yl)hexan-2-yl)-N-methyl-5-(4-methylpiperazin-1-yl)-1,3,4-thiadiazole-2-carboxamide |
| 25 | 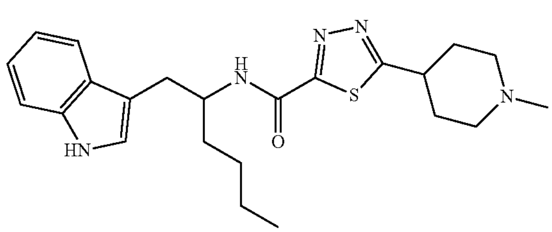 [SMILES: CCCCC(Cc1c[nH]c2ccccc12)NC(=O)c1nnc(C2CCN(C)CC2)s1] | N-(1-(1H-indol-3-yl)hexan-2-yl)-5-(1-methylpiperidin-4-yl)-1,3,4-thiadiazole-2-carboxamide |

| Ex. | Structure | Chemical Name |
|---|---|---|
| 26 | | N-(1-(1H-indol-3-yl)hexan-2-yl)-2-(4-methyl-1,4-diazepan-1-yl)thiazole-5-carboxamide | and pharmaceutically acceptable salts thereof.

In other embodiments, the compound of Formula (I) is selected from the group consisting of:

| Ex. | Structure | Chemical Name |
|---|---|---|
| 27 | 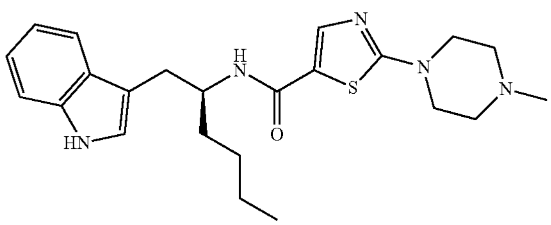 [SMILES: CCCC[C@@H](Cc1c[nH]c2ccccc12)NC(=O)c1cnc(N2CCN(C)CC2)s1] | (S)-N-(1-(1H-Indol-3-yl)hexan-2-yl)-2-(4-methylpiperazin-1-yl)thiazole-5-carboxamide |
| 28 | | (R)-N-(1-(1H-Indol-3-yl)hexan-2-yl)-2-(4-methylpiperazin-1-yl)thiazole-5-carboxamide | and pharmaceutically acceptable salts thereof.

In some embodiments, the compound of Formula (I) is selected from the group consisting of Examples 1-11, and pharmaceutically acceptable salts thereof. In other embodiments, the compound is a hydrochloride salt form. In other embodiments, the compound is Example 27 or 28, or a pharmaceutically acceptable salt thereof. In other embodiments, $R^2$ of Formula (I) is in the (S) stereochemical configuration. In other embodiments, $R^2$ of Formula (I) is in the (R) stereochemical configuration.

Chemical Definitions

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

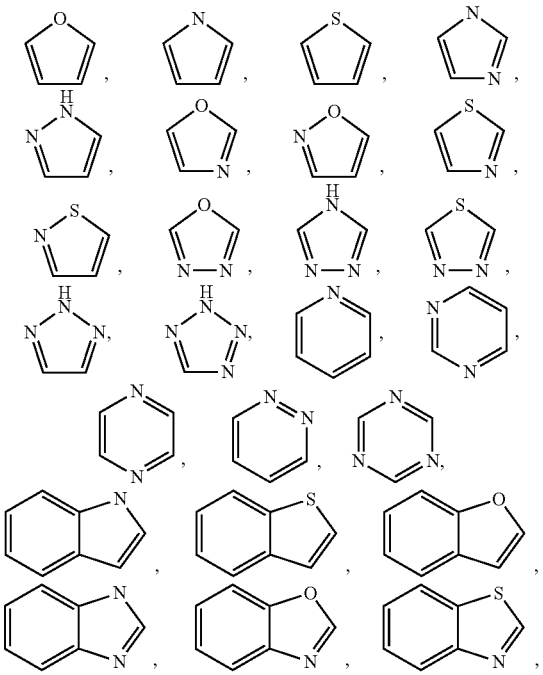

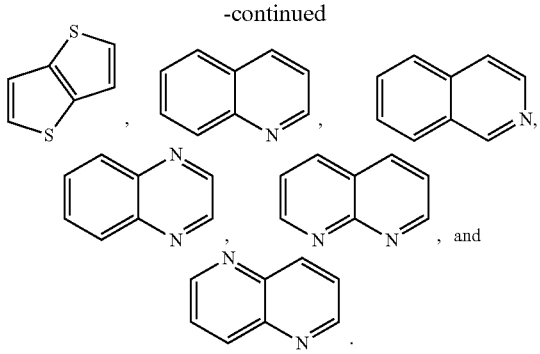

The term "halogen" represents chlorine, fluorine, bromine, or iodine. The term "halo" represents chloro, fluoro, bromo, or iodo.

The term "oxo" represents a carbonyl oxygen. For example, a cyclopentyl substituted with oxo is cyclopentanone.

Those skilled in the art will recognize that the species listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," *NeuroRx* 2005, 2(2), 226-236, and references cited therein. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The invention also includes pharmaceutically acceptable salts of the compounds represented by Formula (I), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula (I) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.01 to about 50 mg/kg daily, or from about 0.05 to about 20 mg/kg daily, or from about 0.1 to about 10 mg/kg daily. Additional dosages include from about 0.1 mg to 1 g daily, from about 1 mg to about 10 mg daily, from about 10 mg to about 50 mg daily, from about 50 mg to about 250 mg daily, or from about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary neurodegenerative diseases that are characterized by protein aggregation include Alzheimer's Disease, Parkinson's Disease, fronto-temporal Dementia, Dementia with Lewy Bodies (Lewy body disease), Parkinson's Disease with Dementia, Multiple System Atrophy, Amyotrophic Lateral Sclerosis, and Huntington's Disease, as well as cancers and inflammatory diseases.

In one aspect, the compounds and pharmaceutical compositions of the invention specifically target α-synuclein, β-amyloid, and/or tau protein aggregates. Thus, these compounds and pharmaceutical compositions can be used to prevent, reverse, slow, or inhibit aggregation of α-synuclein, β-amyloid, and/or tau proteins, and are used in methods of the invention to treat degenerative neurological diseases related to or caused by aggregation, e.g., such as aggregation of α-synuclein, β-amyloid, and/or tau proteins. Preferably, the methods of the invention target neurodegenerative diseases associated with aggregation of α-synuclein, β-amyloid, and/or tau protein. In preferred embodiments, methods of treatment target Parkinson's disease, Alzheimer's disease, Lewy body disease, or multiple system atrophy. In other embodiments, the methods target cancer or melanoma. The compounds, compositions, and method of the present invention are also used to mitigate deleterious effects that are secondary to protein aggregation, such as neuronal cell death.

In some aspects, the compounds, compositions, and methods of the invention are used to target α-synuclein (SYN) aggregation. In alternative aspects, the compounds, compositions, and methods of the invention are used to target Aβ aggregation.

In the inhibitory methods of the invention, an "effective amount" means an amount sufficient to reduce, slow the progression of, or reverse protein or peptide aggregation. Measuring the amount of aggregation may be performed by routine analytical methods such as those described below. Such modulation is useful in a variety of settings, including in vitro assays. In such methods, the cell is preferably a nerve cell.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 ug to 2 mg of active agent per kilogram of subject's body weight per day, preferably about 0.05 to 100 mg/kg/day, or about 1 to 35 mg/kg/day, or about 0.1 to 10 mg/kg/day. In alternative embodiments an exemplary dose is in the range of about 1 mg to about 1 g per day, or about 1-500, 1-250, 1-100, 1-50, 50-500, or 250-500 mg per day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of neurodegenerative disorders. Further additional active ingredients for cancer applications include other cancer therapeutics or agents that mitigate adverse effects of cancer chemotherapeutic agents. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating neurodegenerative disorders, including those active against another target associated with the disease, such as but not limited to, a) compounds that address protein misfolding (such as drugs which reduce the production of these proteins, which increase their clearance or which alter their aggregation and/or propagation); b) compounds that treat symptoms of such disorders (e.g., dopamine replacement therapies); and c) drugs that act as neuroprotectants by complementary mechanisms (e.g., those targeting autophagy, those that are anti-oxidants, and those acting by other mechanisms such as adenosine A2A antagonists).

For example, compositions and formulations of the invention, as well as methods of treatment, can further comprise other drugs or pharmaceuticals, e.g., other active agents useful for treating or palliative for a degenerative neurological disease related to or caused by protein aggregation, e.g., synuclein, beta-amyloid and/or tau protein aggregation, e.g., Parkinson's disease, Alzheimer's Disease (AD), Lewy body disease (LBD) and multiple system atrophy (MSA), or related symptoms or conditions. For example, the pharmaceutical compositions of the invention may additional comprise one or more of such active agents, and methods of treatment may additionally comprise administering an effective amount of one or more of such active agents. In certain embodiments, additional active agents may be antibiotics (e.g., antibacterial or bacteriostatic peptides or proteins), e.g., those effective against gram positive or negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. Additional active agents include those useful in such compositions and methods include dopamine therapy drugs, catechol-O-methyl transferase (COMT) inhibitors, monamine oxidase inhibitors, cognition enhancers (such as acetylcholinesterase inhibitors or memantine), adenosine 2A receptor antagonists, beta-secretase inhibitors, or gamma-secretase inhibitors. In particular embodiments, at least one compound of the present invention may be combined in a pharmaceutical composition or a method of treatment with one or more drugs selected from the group consisting of: tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1,2-benzisoxazol-6-one maleate), ER-127528 (4-[(5,6-dimethoxy-2-fluoro-1-indanon)-2-yl]methyl-1-(3-fluorobenzyl)piperidine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)-R-.alpha.-[[2-(dimethylamino)ethoxy]methyl] benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methanamine), SDZ-220-581 ((S)-alpha-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyridine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl)piperazin-1-yl)pyrimidine dihydrochloride hydrate), or a combination thereof.

Potential combination agents for cancer therapies may include, for example, protein and lipid kinase inhibitors (e.g., PI3K, B-raf, BCR/ABL), radiation treatment enhancers, microtubule binders (e.g., taxol, vinblastine), cell metabolism inhibitors, DNA intercalators, topoisomerase inhibitors (e.g., doxorubicin), and DNA alkylating agents.

Assays

The compounds described herein can be used in research applications, including in in vitro, in vivo, or ex vivo experimental systems. Experimental systems can include, without limitation, cell samples, tissue samples, cell components or mixtures of cell components, whole or partial organs, or organisms. Research applications include, without limitation, use as assay reagents, elucidation of biochemical pathways, or evaluation of the effects of other agents on the experimental system in the presence or absence of one or more compounds described herein.

The compounds described herein can also be used in biochemical assays. In some embodiments, a compound described herein can be incubated with a tissue or cell sample from a subject to evaluate the subject's potential response to administration of the compound, or to determine which compound described herein produces the optimum effect in a specific subject or set of subjects. One such assay would involve (a) obtaining a cell sample or tissue sample from a subject in which modulation of one or more biomarkers can be assayed; (b) administering one or more compounds described herein to the cell sample or tissue sample; and (c) determining the amount of modulation of the one or more biomarkers after administration of the compound, compared to the status of the biomarker prior to administration of the compound. Optionally, following step (c), the assay would involve an additional step (d) selecting a compound for use in treating a disease or medical condition associated with protein aggregation based on the amount of modulation determined in step (c).

Chemical Synthesis

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I). Isotopically labeled compounds as described herein are prepared according to the methods described below, using suitably labeled starting materials. Such materials are generally available from commercial suppliers of radiolabeled chemical reagents.

Scheme A

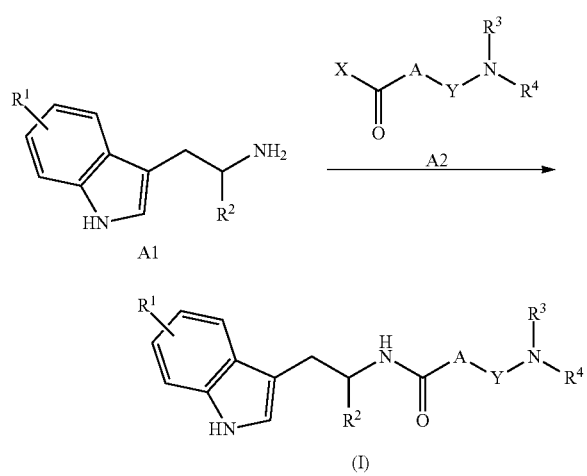

Compounds of Formula (I) are prepared as shown in Scheme A. Amino-ethyl indole derivatives A1 are commercially available or are prepared according to Scheme B. Compounds A1 are coupled with activated acyl compounds A2, wherein X is, for example, —OH or —Cl, under standard amide formation conditions to produce compounds of Formula (I).

Scheme B

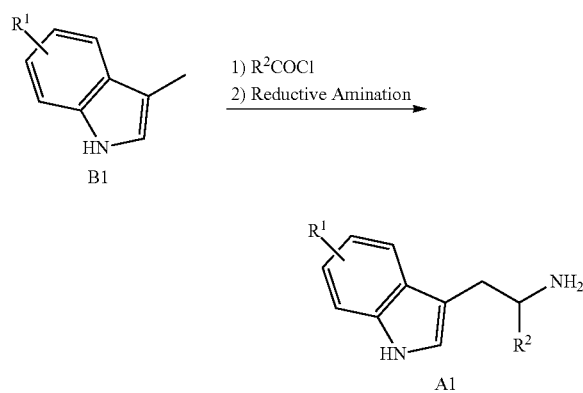

As shown in Scheme B, substituted indoles A1 are prepared from methyl-indoles B1 by acylation followed by reductive amination.

Scheme C

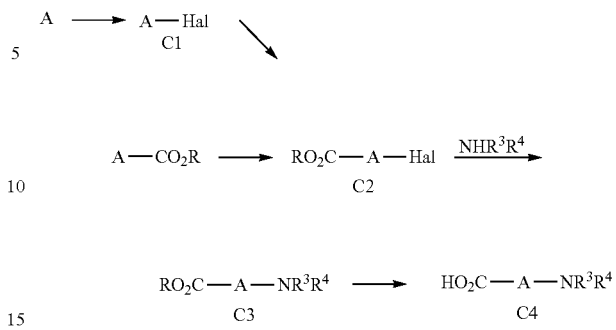

Heterocyclic compounds C4 are prepared according to Scheme C. Certain compounds A, C1, A-CO$_2$R (where R is H or C$_{1-4}$alkyl), and C2 are commercially available. In some embodiments, heterocycles A are halogenated to form halo compounds C1, and then are acylated to form bis-functionalized compounds C2. In other embodiments, compounds A-CO$_2$R are halogenated to form compounds C2. Coupling with amines HNR$^3$R$^4$ under standard amide coupling conditions provides compounds C3. Hydrolysis of esters C3 yields amino acids C4, which can be used in coupling reactions as shown in Scheme A.

Scheme D

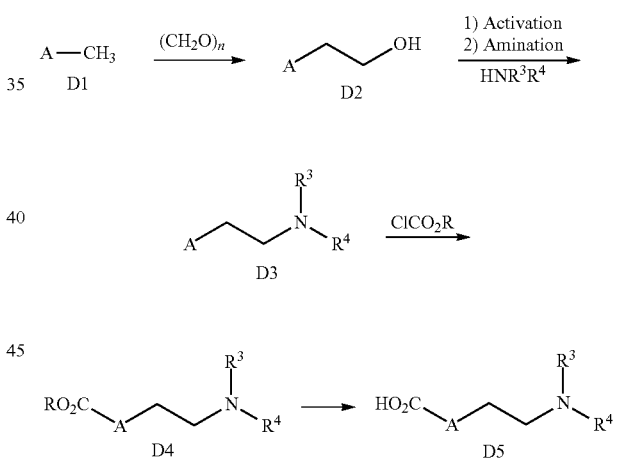

As shown in Scheme D, methyl-heterocyclic compounds D1 are homologated with, for example, paraformaldehyde, to provide hydroxyethyl compounds D2. Activation of the hydroxyl group as, for example, a halide or tosylate, and displacement with HNR$^3$R$^4$, yields amino compounds D3. Acylation of the heterocyclic ring gives esters D4, and hydrolysis generates amino acids D5.

EXAMPLES

The following examples are offered to illustrate but not to limit the invention. One of skill in the art will recognize that the following synthetic reactions and schemes may be modified by choice of suitable starting materials and reagents in order to access other compounds of Formula (I).

Example 1: N-(1-(1H-Indol-3-yl)hexan-2-yl)-2-(4-methylpiperazin-1-yl)thiazole-5-carboxamide

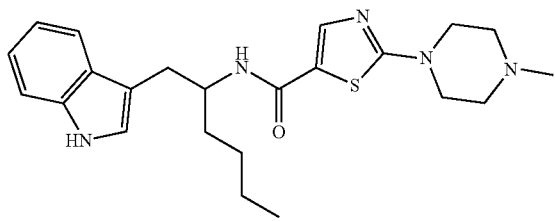

Step 1.

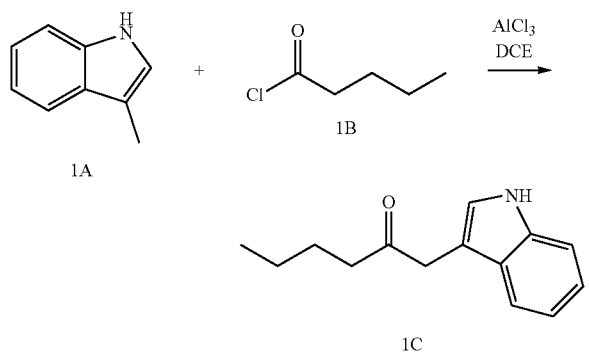

To a solution of compound 1A (6 g, 45.8 mmol) in dry 1,2-dichloroethane (80 mL) was added AlCl$_3$ (18.3 g, 137.4 mmol) at 0° C. The mixture was warmed to 25° C. and stirred for 30 min. The mixture was cooled to 0° C., and compound 1B (6.2 g, 51.3 mmol) was added dropwise. The mixture was stirred at 25° C. for 48 h. The reaction mixture was poured into ice water slowly and extracted with dichloromethane (DCM, three times (3×)). The organic layer was washed with brine (3×), dried over Na$_2$SO$_4$ and concentrated. The residue was purified by column (20:1 petroleum ether/EtOAc) to give compound 1C (4.8 g, 49%) as a yellow solid. $^1$H NMR (400 MHz, CDCl$_3$) δ 8.16 (br s, 1H), 7.39 (d, J=8.0 Hz, 1H), 7.37 (d, J=8.0 Hz, 1H), 7.23 (t, J=7.2 Hz, 1H), 7.15 (t, J=7.2 Hz, 1H), 7.15 (s, 1H), 3.83 (s, 2H), 2.50 (t, J=8.8 Hz, 2H), 1.54-1.63 (m, 2H), 1.24-1.29 (m, 2H), 0.86 (t, J=7.6 Hz, 3H).

Step 2.

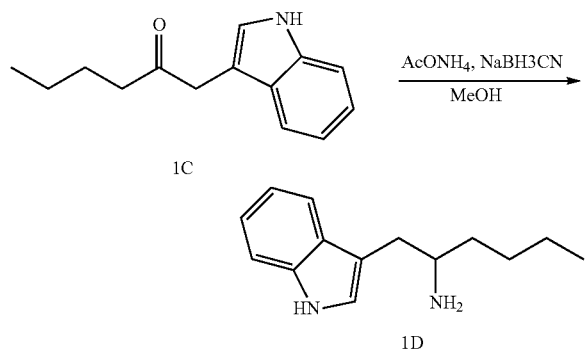

A mixture of compound 1C (4.8 g, 22.3 mmol) in MeOH (150 mL) was added AcONH$_4$ (3.35 g, 44.6 mmol) and NaBH$_3$CN (2.8 g, 44.6 mmol). The mixture was refluxed for 24 h. The mixture was concentrated, and the residue dissolved in DCM (150 mL), washed with brine (3×), dried over Na$_2$SO$_4$, and concentrated to give crude compound 1D (2.4 g, 50%) as a yellow solid. $^1$H NMR (400 MHz, CDCl$_3$) δ 8.09 (s, 1H), 7.54 (d, J=8.0 Hz, 1H), 7.29 (d, J=8.0 Hz, 1H), 7.03-7.18 (m, 2H), 6.98 (s, 1H), 3.01-3.03 (m, 1H), 2.89 (dd, J=14.0, 4.0 Hz, 1H), 2.52 (dd, J=14.0, 8.8 Hz, 1H), 1.18-1.50 (m, 8H), 0.85 (t, J=7.2 Hz, 3H).

Step 3.

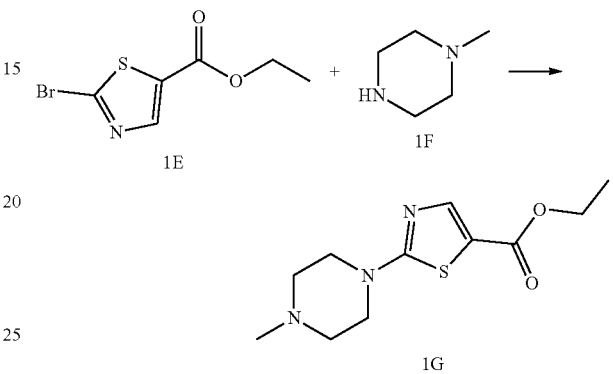

A mixture of compound 1E (2.2 g, 10.0 mmol), N-methylpiperazine (1.1 g, 11.0 mmol), and K$_2$CO$_3$ (3.4 g, 24.9 mmol) in acetonitrile (70 mL) was stirred at 80° C. for 24 h. The mixture was concentrated and diluted with H$_2$O and extracted with EtOAc (3×). The combined organic layers were dried and then concentrated to give compound 1G (2.5 g, >100%) as a brown solid. $^1$H NMR (400 MHz, CDCl$_3$) δ 7.85 (s, 1H), 4.28 (q, J=7.2 Hz, 2H), 3.58 (t, J=5.6 Hz, 4H), 2.50 (t, J=5.6 Hz, 4H), 2.33 (s, 3H), 1.32 (t, J=7.2 Hz, 3H).

Step 4.

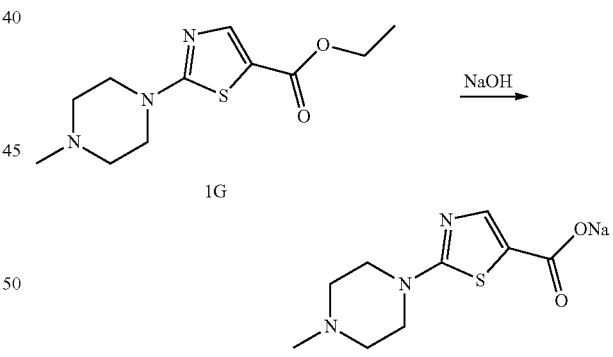

A mixture of compound 1G (2.0 g, 8.3 mmol) in THF (20 mL) was added solution of NaOH (1.33 g, 33.2 mmol) in H$_2$O (40 mL). The mixture was stirred for 24 h at 80° C. The mixture was concentrated to remove THF and extracted with n-BuOH. The organic layer was dried and concentrated to give compound 1H (1.38 g, 66.7%) as a white solid. $^1$H NMR (400 MHz, MeOD) δ 7.55 (s, 1H), 3.49-3.52 (m, 4H), 2.53-2.56 (m, 4H), 2.36 (s, 3H).

Step 5.

To a mixture of compound 1H (1.1 g, 5.1 mmol) in CH$_2$Cl$_2$ (50 mL) and THF (5 mL) was added compound 1D (2 g, 8.09 mmol), followed by benzotriazol-1-yl-oxytripyrrolidinophosphonium hexafluorophosphate (PyBOP, 3.18 g, 6.12 mmol) and DIPEA (2.6 g, 20.4 mmol). After 24 h at 25° C. under N₂, the mixture was diluted with H₂O (40 mL) and extracted with DCM (3×). The combined organic layers were dried over Na₂SO₄, concentrated, and the residue purified by preparative-HPLC (Shimadzu LC-8A Preparative HPLC, Luna(2) C18 column, 26%-56% acetonitrile in NH₄OAc over 20 min at 80 mL/min) to give Example 1 (576 mg, 27%) as a white solid. ¹H NMR (400 MHz, CDCl₃) δ 8.23 (s, 1H), 7.39 (1H, s), 7.38 (d, J=7.2 Hz, 1H), 7.22 (d, J=7.2 Hz, 1H), 7.07-7.21 (m, 2H), 7.06 (s, 1H), 5.50 (d, J=8.4 Hz, 1H), 4.40-4.46 (m, 1H), 3.56 (t, J=5.2 Hz, 4H), 3.0-3.1 (m, 2H), 2.52 (t, J=4.8 Hz, 4H), 2.36 (s, 3H), 1.26-1.60 (m, 6H), 0.88 (t, J=7.2 Hz, 3H). LCMS: 100% (M+1+): 426.2.

Alternate Synthesis

To a mixture of compound 3A (400 g, 0.98 mol, see below) and K₂CO₃ (340 g, 2.5 mol) in CH₃CN (3 L) was added compound 1F (197 g, 1.97 mol). The mixture was stirred for 12 h at 80° C. under N₂ atmosphere. The mixture was diluted with water (4 L) and extracted with DCM (4 L×3). The combined organic layers were dried over Na₂SO₄ and concentrated. The residue was washed with 1:1 petroleum ether/ethyl acetate to give Example 1 (200 g, 44%) as a white solid. 4 M HCl in ethyl acetate (235 mL) was added to a solution of Example 1 (200 g, 0.47 mol) in DCM (2 L). The mixture was stirred for 1 h at room temperature, the solvent was concentrated, and the residue was recrystallized from methyl t-butyl ether (1 L). The resultant solid was collected by filtration and dried under reduced pressure at 50° C. to give the HCl salt of Example 1 (210 g, 92%).

Example 2: N-(2-(1H-Indol-3-yl)ethyl)-2-(4-methylpiperazin-1-yl)thiazole-5-carboxamide

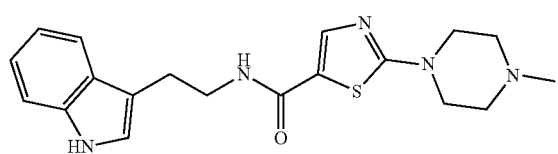 [SMILES: CN1CCN(c2ncc(C(=O)NCCc3c[nH]c4ccccc34)s2)CC1]

Step 1.

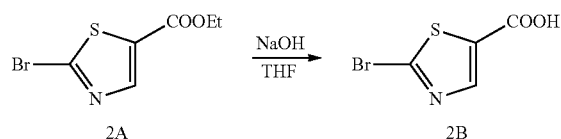 [SMILES: CCOC(=O)c1cnc(Br)s1 ; "NaOH" ; O=C(O)c1cnc(Br)s1 ; "THF"]

A solution of NaOH (4.1 g, 102 mmol) in H₂O (100 mL) was added dropwise to a solution of compound 2A (20 g, 84.7 mmol) in tetrahydrofuran (THF, 100 mL) at 0° C. The mixture was stirred at 10° C. for 1 h. The mixture was neutralized with HCl (6 M) and extracted with EtOAc (3×). The organic layer was washed by brine, dried over Na₂SO₄, and concentrated to give compound 2B (17.7 g, 100%) as a yellow solid. ¹H NMR (400 MHz, DMSO-d₆) δ 8.21 (s, 1H).

Step 2.

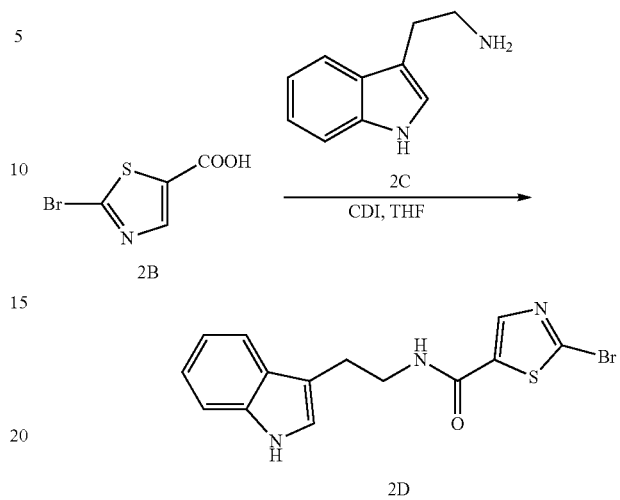

1,1-Carbonyl-diimidazole (2.06 g, 12.75 mmol) was added to a mixture of compound 2B (2.6 g, 12.5 mmol) in THF (16 mL). The mixture was stirred for 1 h at room temperature, and then was treated with triethylamine (TEA, 2.53 g, 25 mmol) and compound 2C (2 g, 12.5 mmol). The resulting mixture was stirred at room temperature for 12 h. The mixture was diluted with EtOAc, washed with 1M HCl (2×) and brine, then dried over Na₂SO₄, and concentrated to give compound 2D (4.41 g, >100%) as a yellow solid.

Step 3.

To a mixture of compound 2D (1 g, 5.7 mmol) and K₂CO₃ (1.0 g, 7.2 mmol) in CH₃CN (6 mL) was added N-methylpiperazine (0.6 g, 5.7 mmol). The mixture was stirred for 12 h at 80° C. under N₂ atmosphere. Water was added and the mixture was extracted with DCM (5×). The combined organic layers were dried over Na₂SO₄ and concentrated to give a yellow solid (0.8 g), which was washed with methyl tertiary butyl ether (5 mL) to give Example 2 (0.3 g, 29%) as a white solid. ¹H NMR (400 MHz, DMSO-d₆) δ 8.37 (m, 1H), 7.78 (s, 1H), 7.56 (d, J=7.6 Hz, 1H), 7.40 (d, J=8.4 Hz, 1H), 7.38-7.35 (m, 2H), 7.16 (s, 1H), 7.07 (t, J=7.4 Hz, 1H), 6.98 (t, J=7.4 Hz, 1H), 3.48-3.44 (m, 6H), 2.90 (t, J=7.2 Hz, 2H), 2.42-2.39 (m, 2H), 2.22 (s, 3H). MS: (M+H⁺): 370.

Example 3: N-(1-(1H-Indol-3-yl)hexan-2-yl)-2-(piperazin-1-yl)thiazole-5-carboxamide

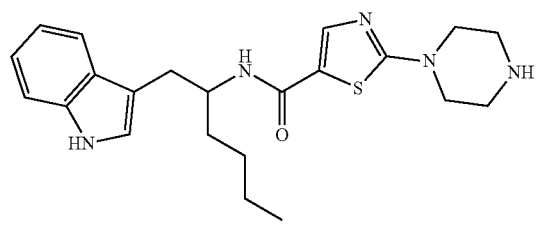 [SMILES: CCCCC(Cc1c[nH]c2ccccc12)NC(=O)c1cnc(N2CCNCC2)s1]

Step 1.

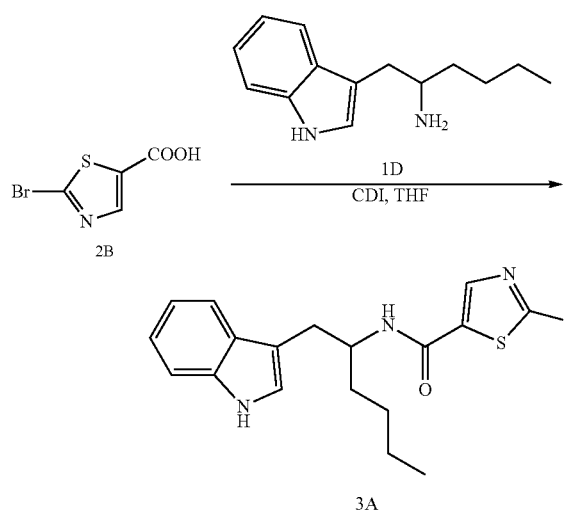

1,1-Carbonyl-diimidazole (4.04 g, 24.96 mmol) was added to a mixture of compound 2B (5.19 g, 24.96 mmol) in THF (40 mL). The mixture was stirred for 1 h at room temperature and then was treated with TEA (7.56 g, 74.88 mmol) and compound 1D (5.4 g, 24.96 mmol). After 12 h at room temperature, the mixture was diluted with EtOAc, washed successively with 1 M HCl (2×) and brine, dried over $Na_2SO_4$, and concentrated to give compound 3A (7.74 g, 76%) as a yellow solid. $^1$H NMR (400 MHz, MeOD-$d_4$) δ 8.36 (d, 1H, J=8.4 Hz), 7.97 (s, 1H), 7.56 (d, J=8 Hz, 1H), 7.30 (d, J=8 Hz, 1H), 7.06 (t, J=7.2 Hz, 1H), 7.05 (s, 1H), 6.95 (t, J=7.2 Hz, 1H), 4.31-4.28 (m, 1H), 3.0-2.97 (m, 1H), 1.75-1.50 (m, 2H), 1.45-1.25 (m, 4H), 2.22 (t, J=6.8 Hz, 3H). MS: (M+H$^+$): 406, 408.

Step 2.

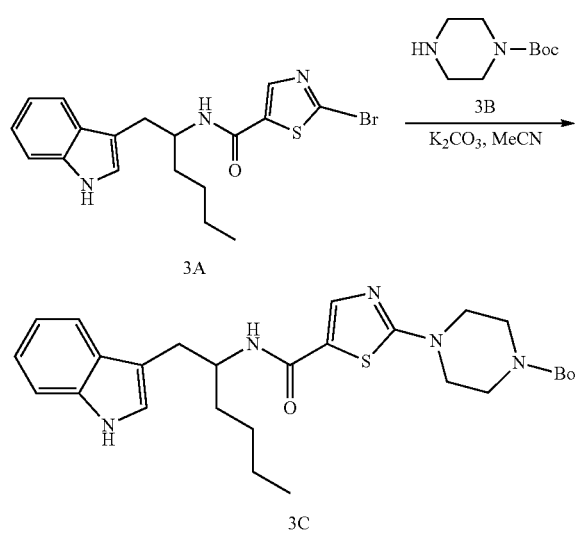

To a mixture of compound 3A (2 g, 5.7 mmol) and $K_2CO_3$ (1.77 g, 12.8 mmol) in $CH_3CN$ (12 mL) was added compound 3B (0.92 g, 4.9 mmol). After 12 h at 80° C. under $N_2$ atmosphere, water was added (30 mL) and the mixture was extracted with EtOAc (3×). The combined organic layers were dried over $Na_2SO_4$, concentrated, and purified by column chromatography (10 to 67% EtOAc/petroleum ether) to give compound 3C (2 g, 79%) as a yellow solid. This compound was used directly in the next step without characterization.

Step 3.

A solution of compound 3C (1 g, 2.0 mmol) in methanol (10 mL) was treated with HCl (10 mL, 4 M in methanol). After stirring at room temperature for 3 h, the solvent was removed and the residue was poured into ice water (20 mL), adjusted pH to 9 with $NaHCO_3$, and extracted with EtOAc (2×). The combined organic layers were dried over $Na_2SO_4$ and concentrated to give a yellow solid (0.45 g). Purification by column chromatography (petroleum ether/DCM/MeOH 50/50/0 to 0/90/10) gave Example 3 (0.32 g, 39%) as a white solid. $^1$H NMR (400 MHz, CDCl$_3$) δ 8.16 (s, 1H), 7.64 (d, J=7.6 Hz, 1H), 7.39-7.36 (m, 2H), 7.18 (t, J=7.6 Hz, 1H), 7.13 (t, J=7.6 Hz, 1H), 7.05 (s, 1H), 5.53 (d, J=8.8 Hz, 1H), 4.46-4.38 (m, 1H), 3.58-3.49 (m, 4H), 3.06-2.96 (m, 6H), 2.05 (s, 1H), 1.65-1.60 (m, 1H), 1.48-1.32 (m, 5H), 0.90-0.86 (m, 3H). MS: (M+H$^+$): 412.

Example 4: N-(2-(1H-Indol-3-yl)ethyl)-2-(2-(4-methylpiperazin-1-yl)ethyl)thiazole-5-carboxamide

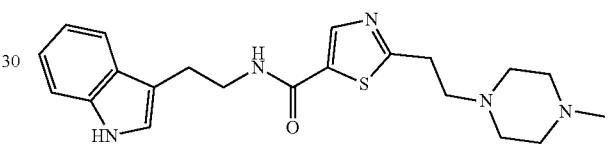

Step 1.

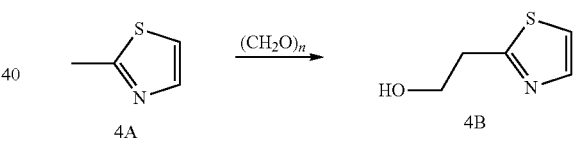

A mixture of compound 4A (50 g, 0.5 mol) and paraformaldehyde (50 g) in a sealed tube was stirred at 140° C. for 3 h. The reaction mixture was purified by column chromatography (50% DCM/EtOAc) to give compound 4B (27 g, 41%) as a light yellow oil. $^1$H NMR (400 MHz, CDCl$_3$) δ 7.62 (s, 1H), 7.16 (s, 1H), 3.91-3.98 (m, 2H), 3.23-3.28 (m, 2H).

Step 2.

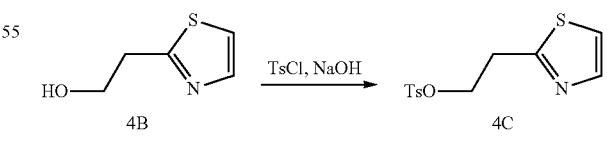

To a solution of compound 4B (27 g, 0.2 mmol) in THF (100 mL) was added a solution of NaOH (16.7 g, 0.4 mol) in water (100 mL) at 0° C. After stirring for 10 min, 4-methylbenzene-1-sulfonyl chloride (59.5 g, 0.3 mol) was added portionwise. The mixture was allowed to warm to room temperature and was stirred a total of 2 h. The mixture was extracted with EtOAc (3×). The organic phase was washed with brine, dried over Na₂SO₄, concentrated, and purified by column chromatography (hexane/EtOAc=2:1) to give compound 4C (32 g, 54%) as a colorless oil. ¹H NMR (400 MHz, CDCl₃) δ 7.75 (2H, d, J=8 Hz, 2H), 7.65 (1H, d, J=4 Hz, 1H), 7.32 (d, J=8 Hz, 2H), 7.22 (d, J=4 Hz, 1H), 4.40 (t, J=8 Hz, 2H), 3.80 (t, J=8 Hz, 2H), 2.45 (s, 3H).

Step 3.

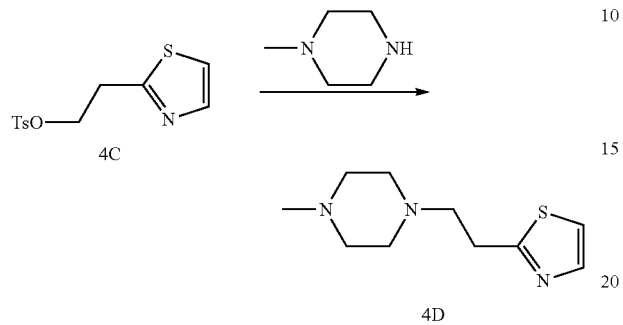

To a solution of compound 4C (32 g, 0.11 mol) in acetonitrile (300 mL) was added N-methylpiperazine (16.9 g, 0.16 mol) and Cs₂CO₃ (55 g, 0.16 mol). The mixture was stirred at 60° C. overnight, then the mixture was filtered and the filtrate was concentrated, the residue was purified by column chromatography (DCM/MeOH=10:1) to give compound 4D (14 g, 47%) as a light yellow oil. ¹H NMR (400 MHz, CDCl₃) δ 7.67 (d, J=3.2 Hz, 1H), 7.19 (d, J=2.4 Hz, 1H), 3.21 (t, J=8.0 Hz, 2H), 2.79 (t, J=8.0 Hz, 2H), 2.59 (s, 4H), 2.50 (s, 4H), 2.31 (s, 3H).

Step 4.

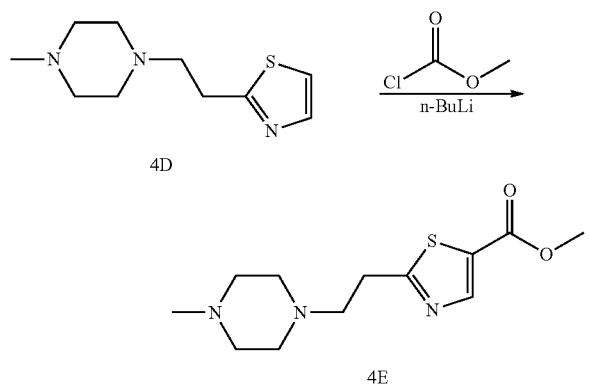

To a solution of compound 4D (14 g, 66 mmol) in anhydrous THF (70 mL) was added n-BuLi (32 mL, 80 mmol) dropwise at −78° C. The mixture was stirred at this temperature for 30 min, then methyl carbonochloridate (7.52 g, 80 mmol) was added dropwise to the solution at the same temperature. The mixture was stirred for 3 h, warming to room temperature during that time. The mixture was diluted with saturated aqueous NH₄Cl (50 mL), extracted with EtOAc, washed with brine, dried over Na₂SO₄, and concentrated to give compound 4E (14 g, 78%). This crude product can be used directly in the next step without further purification. ¹H NMR (400 MHz, CDCl₃) δ 8.26 (s, 1H), 3.89 (s, 3H), 3.19 (t, J=8.0 Hz, 2H), 2.77 (t, J=8.0 Hz, 2H), 2.58 (s, 4H), 2.49 (s, 4H), 2.17 (s, 3H).

Step 5.

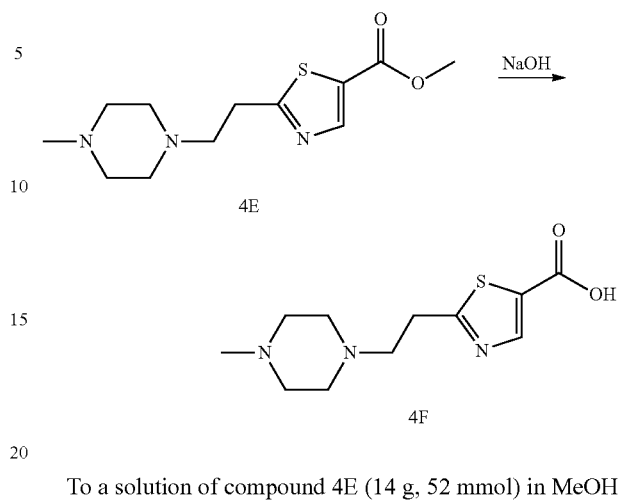

To a solution of compound 4E (14 g, 52 mmol) in MeOH (100 mL) was added a solution of NaOH (3.12 mL, 78 mmol) in water (39 mL). After 3 h at room temperature, the mixture was concentrated and washed with EtOAc (30 mL). The aqueous phase was adjusted to pH=5-6 with 1 N HCl and extracted with EtOAc (3×). The combined organic layers were washed with brine, dried over Na₂SO₄, and concentrated to give compound 4F as an orange solid (12 g, 92%). This crude product can be used directly in the next step without further purification.

Step 6.

A solution of compound 4F (0.8 g, 3.1 mmol) in DCM (2 mL) and THF (10 mL) was treated with 2-chloro-1-methylpyridinium iodide (Mukaiyama reagent, 1.0 g, 3.8 mmol) and N,N-diisopropylethylamine (DIPEA, 1.5 g, 16 mmol) and then stirred for 10 min. The mixture was then treated with 2-(1H-indol-3-yl)ethanamine (0.5 g, 3.1 mmol) and the mixture was stirred at 50° C. for 3 h. The resulting precipitate was filtered off and the filtrate was concentrated in vacuo. The residue was dissolved in ethyl acetate, washed with water (10 mL) and brine (10 mL), dried over Na₂SO₄, and concentrated. The residue was purified by preparative HPLC (Shimadzu LC-8A, Gemini C-18, 12-42% CH₃CN in 0.04% aqueous NH₄OH over 20 min at 80 mL/min) to give Example 4 (200 mg, 16%) as a light yellow solid. ¹H NMR (400 MHz, CDCl₃) δ 8.10 (s, 1H), 7.81 (1H, s, 1H), 7.65 (d, J=8 Hz, 1H), 7.40 (d, J=8 Hz, 1H), 7.21 (t, J=8 Hz, 1H), 7.08 (s, 1H), 5.99 (br s, 1H), 3.77 (q, J=6.2 Hz, 2H), 3.16 (t, J=7.1 Hz, 3H), 3.10 (t, J=6.6 Hz, 2H), 2.75 (t, J=6.8 Hz, 2H), 2.58 (br s, 4H), 2.49 (br s, 4H), 2.32 (s, 3H).

Example 5: N-(1-(1H-Indol-3-yl)hexan-2-yl)-2-(2-(4-methylpiperazin-1-yl)ethyl)thiazole-5-carboxamide

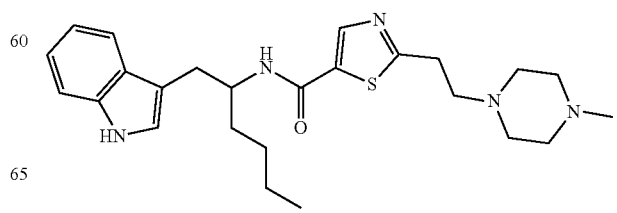

A solution of compound 4F (1.2 g, 5 mmol) in DCM (2 mL) and THF (10 mL) was treated with Mukaiyama reagent (1.65 g, 6.5 mmol) and DIPEA (1.9 g, 20 mmol) and then stirred for 10 min. The mixture was then treated with compound 1D (1.2 g, 5 mmol) and was stirred at 50° C. for 3 h. The resulting precipitate was filtered off and the filtrate was concentrated in vacuo. The residue was dissolved in ethyl acetate (30 mL), washed with water (10 mL) and brine (10 mL), dried over Na$_2$SO$_4$, and concentrated. Purification by preparative HPLC (Shimadzu LC-8A, Gemini C-18, 25-55% CH$_3$CN in 0.04% aqueous NH$_4$OH over 20 min at 80 mL/min) gave Example 5 (250 mg, 14%) as a white solid. $^1$H NMR (400 MHz, CDCl$_3$) δ 8.10 (s, 1H), 7.75 (s, 1H), 7.64 (d, J=8 Hz, 1H), 7.38 (d, J=8 Hz, 1H), 7.19-7.21 (m, 1H), 7.13-7.14 (m, 1H), 5.13 (br s, 1H), 4.41-4.45 (m, 1H), 3.13-3.18 (m, 1H), 3.05-3.09 (m, 1H), 2.74-2.77 (m, 1H), 2.58 (br s, 4H), 2.49 (br s, 4H), 2.32 (s, 3H), 1.63-1.70 (m, 1H), 1.49-1.54 (m, 1H), 1.34-1.39 (m, 4H), 0.89 (t, J=4 Hz, 3H).

Example 6: N-(1-(1H-Indol-3-yl)hexan-2-yl)-2-(4-methylpiperazin-1-yl)oxazole-5-carboxamide

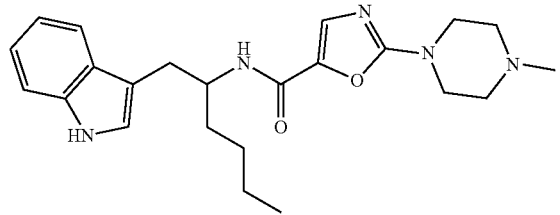

Step 1.

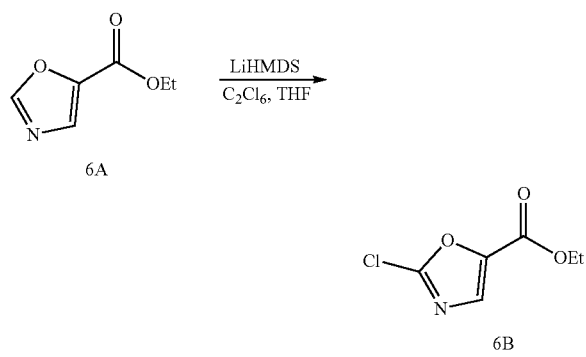

To a solution of compound 6A (15.0 g, 106 mmol) in THF (150 mL) was added dropwise lithium hexamethyl disilazide (178 mL, 170 mmol) at −60° C. The solution was stirred at −50° C. for 1 h. Then hexachloroethane (37.8 g, 160 mmol) was added to the solution. The solution was stirred at room temperature for 12 h. The reaction was quenched by saturated aq. NH$_4$Cl solution (50 mL) and extracted with EtOAc (50 mL). The organic layer was separated, dried over Na$_2$SO$_4$, concentrated under vacuum and the residue was purified with column chromatography to give compound 6B (10 g, 56%) as colorless oil. $^1$H NMR (400 MHz, CDCl$_3$) δ 7.71 (s, 1H), 3.39 (q, J=7.2 Hz, 2H), 1.38 (t, J=7.2 Hz, 3H).

Step 2.

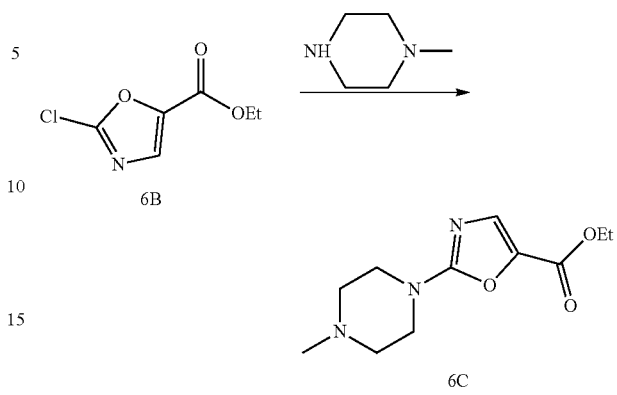

A mixture of compound 6B (5.5 g, 31.3 mmol), N-methylpiperazine (9.4 g, 94 mmol), and K$_2$CO$_3$ (17.3 g, 125.2 mmol) in acetonitrile (80 mL) was heated at reflux at 80° C. for 2 h. The mixture was diluted with H$_2$O and extracted with EtOAc. The organic layer was separated, dried over Na$_2$SO$_4$, and concentrated under vacuum to give compound 6C (7 g, 94%) as a brown oil. $^1$H NMR (400 MHz, CDCl$_3$) δ 7.52 (s, 1H), 4.32 (q, J=7.2 Hz, 2H), 3.66 (t, J=4.8 Hz, 4H), 2.48 (q, J=4.8 Hz, 4H), 2.34 (s, 3H), 1.34 (t, J=7.2 Hz, 3H).

Step 3.

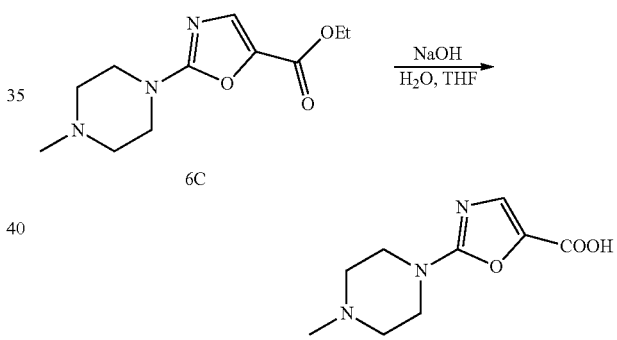

A mixture of compound 6C (2.0 g, 8.4 mmol) and NaOH (0.33 g, 8.4 mmol) in THF (10 mL) and H$_2$O (10 mL) was stirred at room temperature for 2 h. The mixture was concentrated under vacuum to give compound 6D (3.0 g, crude) as a yellow solid. $^1$H NMR (400 MHz, D$_2$O) δ 7.26 (s, 1H), 3.51 (s, 4H), 2.49 (s, 4H), 2.23 (s, 3H).

Step 4.

A mixture of compound 6D (2.0 g, 9.5 mmol), compound 1D (1.64 g, 7.6 mmol), 1-ethyl-3-(3-dimethylaminopropyl)carbodiimide (EDC, 3.63 g, 19 mmol), 1-hydroxy-benzotriazole (HOBt, 2.57 g, 19 mmol), and TEA (1.92 g, 19 mmol) in DMF (30 mL) was stirred at room temperature for 12 h. The mixture was diluted with water and extracted with EtOAc. The organic layer was separated, washed with water (3×), brine, dried over Na$_2$SO$_4$, and concentrated under vacuum. The residue was purified with column chromatography (2 to 10% MeOH/DCM) to give Example 6 (220 mg, 6%) as a white solid. $^1$H NMR (400 MHz CDCl$_3$) δ 8.16 (s, 1H), 7.63 (d, J=8.0 Hz, 1H), 7.40 (s, 1H), 7.39 (t, J=8.0 Hz, 1H), 7.18 (d, J=8.0 Hz, 1H), 7.10 (t, J=8.0 Hz, 1H), 7.08 (s, 1H), 5.69 (d, J=8.8 Hz, 1H), 4.47 (t, J=8.4 Hz, 1H), 3.47 (d, J=2.0 Hz, 4H), 3.08-2.98 (m, 2H), 2.49 (t, J=4.4 Hz, 4H), 2.36 (s, 3H), 1.66-1.51 (m, 1H), 1.51-1.49 (m, 1H), 1.39-1.27 (m, 4H), 0.90 (d, J=7.2 Hz, 3H).

Example 7: N-(1-(1H-Indol-3-yl)hexan-2-yl)-5-(4-methylpiperazin-1-yl)-1,3,4-thiadiazole-2-carboxamide

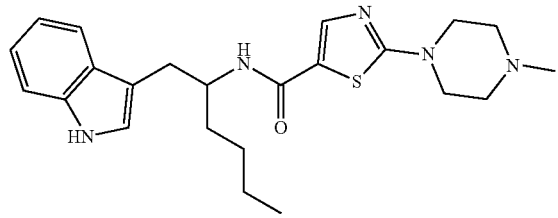 [SMILES: CCCCC(Cc1c[nH]c2ccccc12)NC(=O)c1cnc(N2CCN(C)CC2)o1]

Step 1.

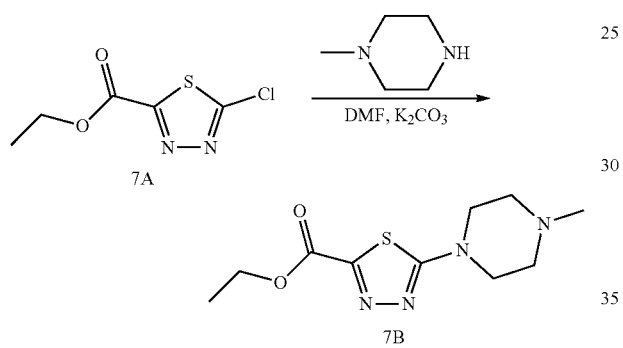

A solution of compound 7A (60 g, 0.313 mol), K$_2$CO$_3$ (130 g, 0.94 mol), and methyl piperazine in DMF (300 mL) was stirred at 40° C. for 3 h. The reaction mixture was poured into water and extracted with CH$_2$Cl$_2$. The organic layer was washed with water, dried over Na$_2$SO$_4$, and concentrated to give compound 7B (58.5 g, 73%) as a yellow solid. $^1$H NMR (400 MHz, CDCl$_3$) δ 4.37-4.47 (m, 2H), 3.60-3.71 (m, 4H), 2.47-2.60 (m, 4H), 2.34 (s, 3H), 1.35-1.47 (m, 3H).

Step 2.

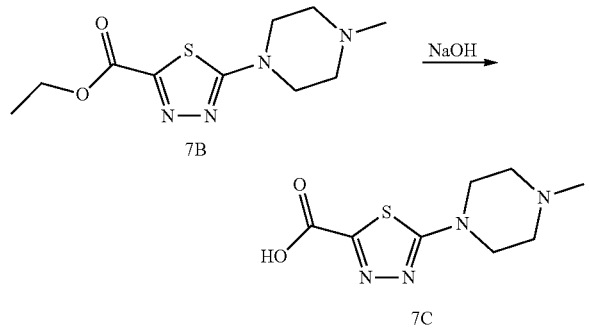

To a solution of compound 7B (5.0 g, 19.53 mmol) in THF (30 mL) was added 1 N aq. NaOH (30 mL) at room temperature and the mixture was stirred for 3 h. The mixture was concentrated to remove THF, adjusted to pH 8 with 1 N aq. HCl, and then freeze-dried to give crude the acid 7C (5.25 g, 100%) as a yellow solid (including NaCl), which was used for next step without any purification. $^1$H NMR (400 MHz, MeOD) δ 3.68 (m, 4H), 2.91 (m, 4H), 2.57 (s, 3H).

Step 3.

To a solution of compound 7C (450 mg, 2 mmol) in DMF (15 mL) and DCM (5 mL) was added EDC (400 mg, 2 mmol) and HOBt (310 mg, 2 mol) at 0° C. The mixture was stirred at 0° C. for 30 min. Compound 1D (500 mg, 2 mmol) was added at 0° C. The mixture was stirred overnight at 40° C. The mixture was diluted with H$_2$O and extracted with EtOAc. The organic layer was dried over Na$_2$SO$_4$ and concentrated to give crude product which was purified by column chromatography (petroleum ether/DCM/MeOH 50/50/0 to 0/10/1) and recrystallization (MeOH) to give Example 7 (230 g, 15%, 2 batches) as an off-yellow solid. $^1$H NMR: (400 MHz, DMSO-d$_6$) δ 10.74 (s, 1H), 8.61 (d, J=8.0 Hz, 1H), 7.56 (d, J=8.0 Hz, 1H), 7.30 (d, J=8.0 Hz, 1H), 7.09 (s, 1H), 7.05-7.02 (m, 1H), 6.96-6.93 (m, 1H), 4.14 (s, 1H), 3.50 (s, 4H), 2.99-2.84 (m, 2H), 2.42 (s, 4H), 2.21 (s, 3H), 1.57 (s, 2H), 1.25-1.21 (m, 4H), 0.80 (s, 3H).

Example 8: N-(1-(1H-Indol-3-yl)hexan-2-yl)-5-(4-methylpiperazin-1-yl)-4H-1,2,4-triazole-3-carboxamide

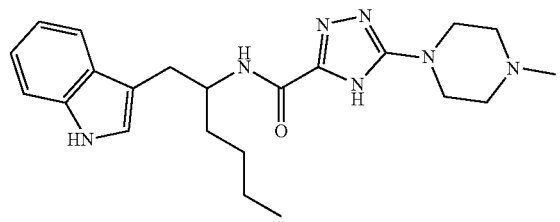 [SMILES: CCCCC(Cc1c[nH]c2ccccc12)NC(=O)c1nnc(N2CCN(C)CC2)[nH]1]

Step 1.

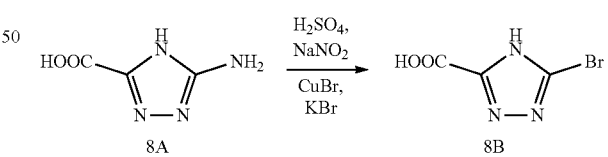

To a stirred mixture of compound 8A (4.5 g, 35 mmol) in 1 M sulfuric acid (70 mL, 70 mmol) was added a solution of sodium nitrite (2.41 g, 52.5 mmol) in water (20 mL) dropwise at 0° C., followed by additional water (35 mL). After 25 min, a solution of KBr (8.33 g, 70 mmol) and copper(I) bromide (4.51 g, 10.5 mmol) in water (35 mL) was added. The resulting mixture was stirred at 20° C. for 3 h and the mixture was extracted with ethyl acetate (3×) and the combined extracts washed with brine (30 mL), dried over Na$_2$SO$_4$, and concentrated to dryness to give compound 8B (2.9 g, 43%) as a white solid. ES-API Found: 191.9, 189.9.

Step 2.

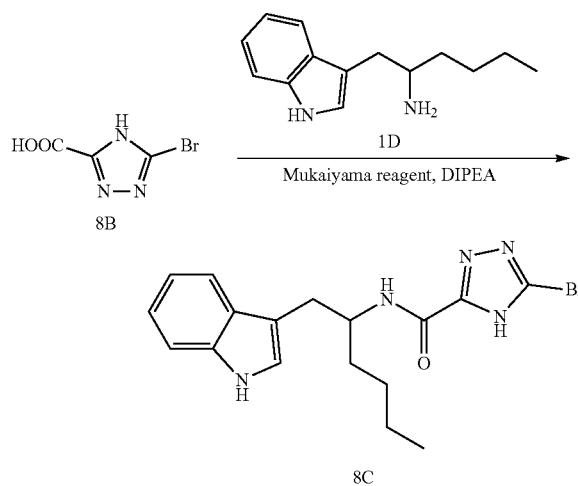

To a solution of compound 8B (2.9 g, 15 mmol) in a mixture of DCM (5 mL) and THF (15 mL) was added Mukaiyama reagent (5 g, 19.5 mmol) and DIPEA (5.8 mL). After stirring for 10 min, 1-(1H-indol-3-yl)hexan-2-amine 1D (3.3 g, 15 mmol) was added to the mixture. The mixture was stirred at 50° C. for 3 h. The mixture was diluted with DCM and washed with water. The organic phase was dried over Na$_2$SO$_4$ and concentrated, and the residue was purified by column chromatography on silica gel (20:1 DCM/MeOH) to give compound 8C (2.7 g, 47%) as a light yellow solid. $^1$H NMR (400 MHz, CDCl$_3$) δ 7.96 (br s, 1H), 7.54 (d, J=8.0 Hz, 1H), 7.23 (d, J=8.0 Hz, 1H), 7.07-7.11 (m, 2H), 7.01-7.04 (m, 1H), 6.96 (br s, 1H), 4.38 (d, J=4 Hz, 1H), 2.95 (d, J=4 Hz, 1H), 1.61 (br s, 1H), 1.39-1.46 (m, 1H), 1.19-1.28 (m, 4H), 0.78 (s, 3H).

Step 3.

A mixture of compound 8C (778 mg, 2 mmol) and N-methylpiperazine (1 g, 10 mmol) was stirred in a sealed tube at 120° C. overnight. Ethyl acetate (20 mL) was added and the precipitated solid was filtered off. The filtrate was washed with water and brine. The solution was dried over Na$_2$SO$_4$, concentrated, and purified by preparative TLC (10:1 DCM/MeOH) to give Example 8 (184 mg, 18%) as a yellow solid. $^1$H NMR (400 MHz, CDCl$_3$) δ 8.43 (br s, 1H), 7.54 (d, J=8.0 Hz, 1H), 7.26 (d, J=8.0 Hz, 1H), 7.19 (s, 1H), 7.05 (t, J=8.0 Hz, 1H), 6.96-7.00 (m, 3H), 4.32 (d, J=4 Hz, 1H), 3.42 (s, 4H), 2.28-2.29 (m, 2H), 2.50 (s, 4H), 2.28 (s, 3H), 1.56-1.62 (m, 1H), 1.41-1.46 (m, 1H), 1.22-1.33 (m, 4H), 0.79 (t, J=8.0 Hz, 3H).

Example 9: N-(1-(1H-Indol-3-yl)hexan-2-yl)-2-(4-methylpiperazin-1-yl)-1H-imidazole-5-carboxamide Step 1.

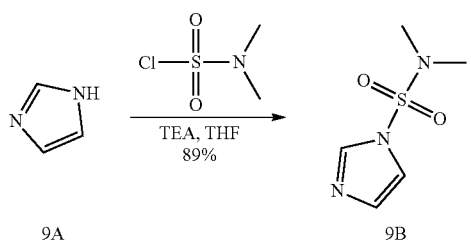

To a solution of imidazole 9A (20 g, 294 mmol) in THF (200 mL) and TEA (40 g, 400 mmol) was added dimethylsulfamoyl chloride (55 g, 383 mmol) slowly at 0° C. The mixture was stirred at room temperature overnight. The reaction mixture was poured into 300 mL of water and extracted with ethyl acetate (3×). The solution was washed with water and brine, dried over Na$_2$SO$_4$, then concentrated to dryness to give compound 9B (42 g, 89%) as a colorless oil, which solidified after standing at room temperature for 1 h. The solid material was used directly in the next step without further purification. $^1$H NMR (400 MHz, CDCl$_3$) δ 7.86 (s, 1H), 7.23 (s, 1H), 7.11 (s, 1H), 2.82 (s, 6H).

Step 2.

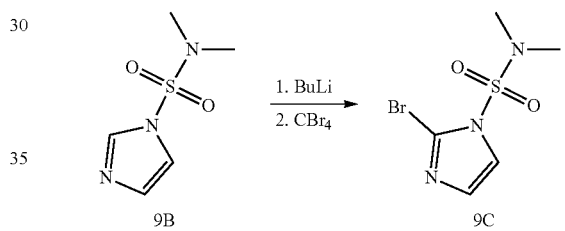

To a solution of compound 9B (10 g, 57 mmol) in anhydrous THF (100 mL) was added n-BuLi (27.3 mL, 68 mmol) dropwise at −78° C. The solution was stirred at this temperature for 30 min. Perbromomethane (20.5 g, 62.7 mmol) was then added at −78° C. and the mixture was allowed to rise to room temperature over a period of 3 h followed by continued stirring at room temperature (25° C.) overnight. The mixture was diluted with satd. aq. NH$_4$Cl (50 mL) and extracted with DCM (3×). The combined organic layers were washed with brine, dried over Na$_2$SO$_4$, and concentrated, and the residue was purified by MPLC (hexane/DCM 1:1) to give compound 9C (8.4 g, 57%) as a light oil. $^1$H NMR (400 MHz, CDCl$_3$) δ 7.41 (s, 1H), 7.00 (s, 1H), 3.01 (s, 6H).

Step 3.

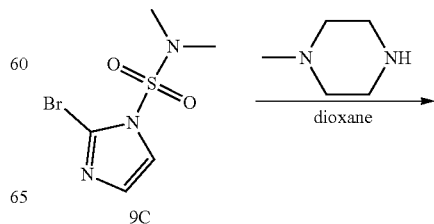

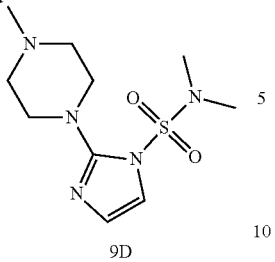

9D

A mixture of compound 9C (10 g, 39 mmol) and N-methylpiperazine (12 g, 118 mmol) in dioxane (100 mL) was stirred at 90° C. overnight. The solution was poured into water and extracted with DCM (3×). The combined organic layers were dried over $Na_2SO_4$ and concentrated and the residue was purified by column chromatography (10:1 DCM/MeOH 10:1) to give compound 9D (3.6 g, 34%) as a brown solid. $^1$H NMR (400 MHz, $CDCl_3$) δ 7.27 (s, 1H), 6.84 (s, 1H), 3.43 (m, 8H), 2.97 (s, 3H), 2.91 (s, 6H).

Step 4.

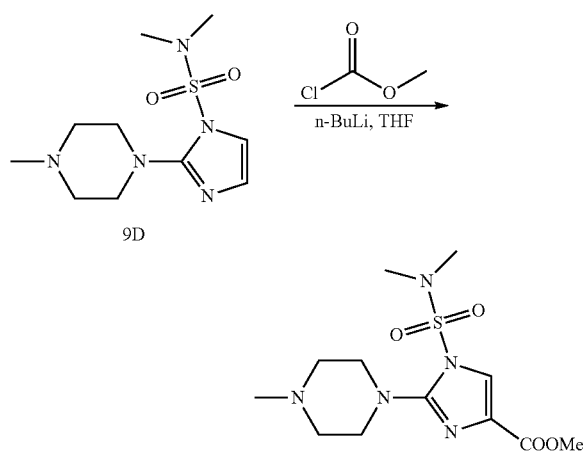

9D

9E

To a solution of compound 9D (3.6 g, 13 mmol) in anhydrous THF (40 mL) was added n-BuLi (6.3 mL, 16 mmol) dropwise at −78° C. The solution was stirred at this temperature for 30 min, and then methyl carbonochloridate (1.48 g, 16 mmol) was added. The mixture was stirred for 3 h at −78° C., and then was allowed to warm to room temperature. The mixture was diluted with satd. aq. $NH_4Cl$ (50 mL) and extracted with DCM (3×). The combined organic layers were dried over $Na_2SO_4$ and concentrated and the residue was purified by column chromatography (60:1 DCM/MeOH) to give compound 9E (1.5 g, 54%) as a brown thick oil. $^1$H NMR (400 MHz, $CDCl_3$) δ 7.29 (s, 1H), 3.76 (s, 3H), 3.50 (m, 4H), 2.77 (s, 6H), 2.51 (m, 4H), 2.28 (s, 3H).

Step 5.

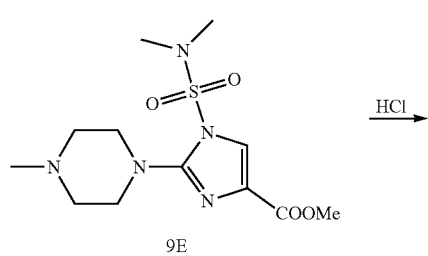

9E

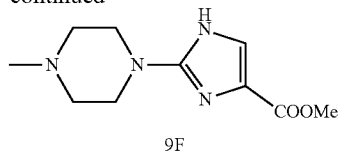

9F

A mixture of compound 9E (1.5 g, 4.5 mmol) and concentrated HCl (7.5 mL) was stirred at 60° C. overnight. The mixture was concentrated under vacuum and the residue was treated with MeOH (10 mL). The white solid that precipitated was collected by filtration and dried under vacuum to give compound 9F (800 mg, 84%) as a hydrochloride salt. $^1$H NMR (400 MHz, $D_2O$) δ 7.53 (s, 1H), 4.09 (d, J=14 Hz, 2H), 3.67 (t, J=12.4 Hz, 2H), 3.59 (d, J=12.4 Hz, 2H), 3.31 (t, J=12.4 Hz, 2H), 2.97 (s, 3H).

Step 6.

To the solution of compound 9F (1.05 g, 5 mmol) in DCM (2 mL) and THF (10 mL) was added Mukaiyama reagent (1.65 g, 6.5 mmol) and DIPEA (1.9 g, 20 mmol). After stirring for 10 min, 1-(1H-indol-3-yl)hexan-2-amine 1D (1.1 g, 5 mmol) was added and the mixture was stirred at 50° C. for 3 h. The solvent was removed under vacuum and the residue was diluted with ethyl acetate and washed with water and brine, dried over $Na_2SO_4$, and concentrated. The residue was purified twice by preparative TLC (10:1 DCM/MeOH) to give Example 9 (200 mg, 8.3%) as a light yellow solid. $^1$H NMR (400 MHz, MeOD-$d_4$) δ 7.59 (d, J=8 Hz, 1H), 7.30 (d, J=8 Hz, 1H), 7.29 (s, 1H), 7.08-7.04 (m, 1H), 7.07 (s, 1H), 6.98-6.94 (m, 1H), 4.33-4.26 (m, 1H), 3.40-3.35 (m, 4H), 2.99-2.97 (m, 2H), 2.70-2.68 (m, 4H), 2.44 (s, 3H), 1.68-1.60 (m, 1H), 1.55-1.45 (m, 1H) 1.38-1.28 (m, 4H), 0.86 (t, J=7 Hz, 3H).

Example 10: N-(1-(5-Fluoro-1H-indol-3-yl)hexan-2-yl)-2-(2-morpholinoethyl)thiazole-5-carboxamide

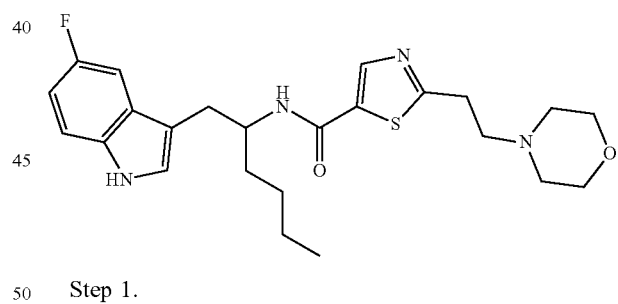

Step 1.

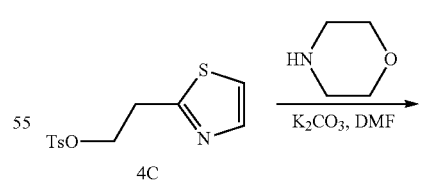

4C

10A

A solution of compound 4C (12.7 g, 44.8 mmol) in acetonitrile (127 mL) was treated with morpholine (5.6 g, 65 mmol) and $Cs_2CO_3$ (21.3 g, 65 mmol) and was stirred at 50°

C. overnight. The mixture was filtered, the filtrate was concentrated, and the residue was purified by column chromatography (CH$_2$Cl$_2$/MeOH=10:1) to give compound 10A (5.6 g, 63%) as a light yellow oil. $^1$H NMR (400 MHz, MeOD) δ 7.66 (d, J=3.2 Hz, 1H), 7.19 (d, J=3.6 Hz, 1H), 3.72 (m, 4H), 3.22 (m, 2H), 2.77 (m, 2H), 2.52 (m, 4H).

Step 2.

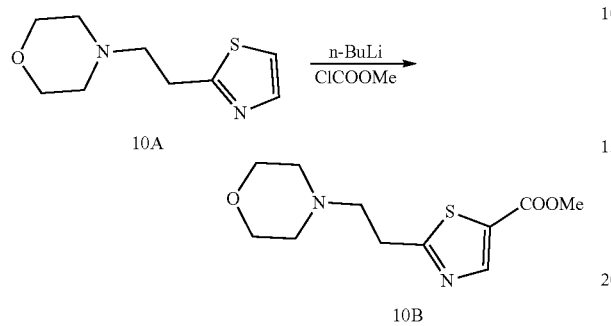

To a solution of compound 10A (5.6 g, 28 mmol) in anhydrous THF (56 mL) was added n-BuLi (13.6 mL, 17 mmol) dropwise at −78° C. The mixture was stirred at this temperature for 30 min and then methyl carbonochloridate (3.2 g, 17 mmol) was added dropwise to the solution at −78° C. The mixture was stirred for 3 h. During this period, the temperature is allowed to rise up to room temperature (25° C.). Saturated NH$_4$Cl aqueous solution (50 mL) was added to quench the reaction. The mixture was extracted with EtOAc, washed with brine, dried over sodium sulfate and concentrated to give compound 10B (4.0 g, 60%). This crude product was used directly in the next step without further purification. $^1$H NMR (400 MHz, CDCl$_3$) δ 8.27 (s, 1H), 3.90 (s, 3H), 3.72-3.76 (m, 4H), 3.21 (t, J=8.0 Hz, 2H), 2.77 (t, J=8.0 Hz, 2H), 2.54 (s, 4H).

Step 3.

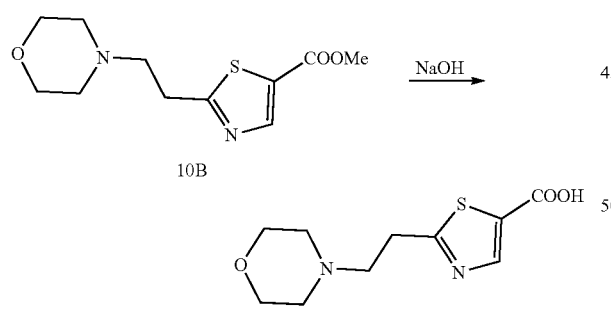

To a solution of compound 10B (3 g, 11.7 mmol) in MeOH (30 mL) was added NaOH (0.7 g, 17 mmol) in water (9 mL). The mixture was stirred at 25° C. for 3 h. MeOH was removed in vacuo and the solution was washed with EtOAc (30 mL). The water phase was adjusted to pH=5-6 with 1 N HCl and extracted with EtOAc (50 mL×3). The organic phase was washed with brine, dried over sodium sulfate and concentrated to dryness to give compound 10C as an orange solid (3 g, 100%). This crude product was used directly in the next step without further purification.

Step 4.

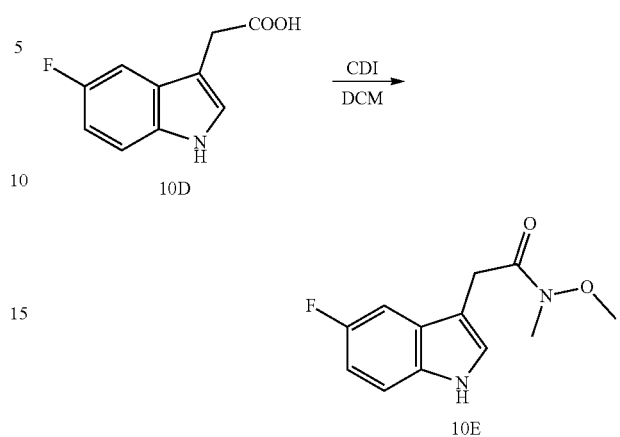

To a solution of compound 10D (3.5 g, 18 mmol) in CH$_2$Cl$_2$ (35 mL) was added CDI (3.52 g, 21.8 mmol). The mixture was stirred at room temperature for 2 h and then N,O-dimethylhydroxylamine hydrochloride (2.3 g, 26 mmol) was added to the mixture. The mixture was stirred for 4 h at room temperature. The mixture was diluted with water (30 mL) and extracted with EtOAc (50 mL×2). The organic phase was washed with brine, dried over sodium sulfate, concentrated to give compound 10E (4.5 g, 100%) as brown oil. H NMR (400 MHz, CDCl$_3$) δ 8.33 (s, 1H), 7.15-7.30 (m, 3H), 6.90-6.92 (m, 1H), 3.87 (s, 2H), 3.73 (s, 3H), 3.28 (s, 3H).

Step 5.

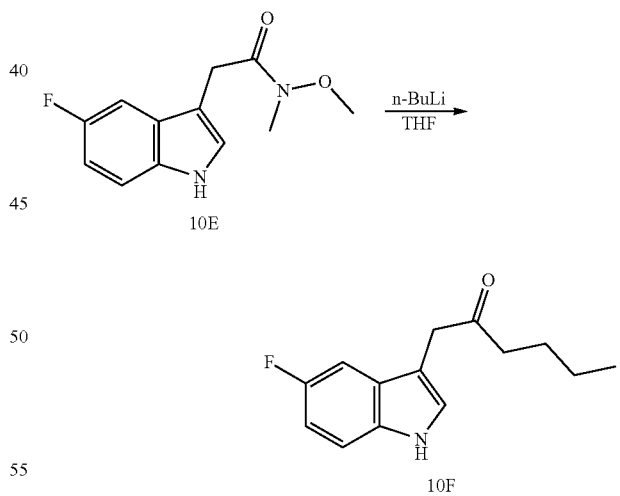

To a solution of compound 10E (3.57 g, 15 mmol) in anhydrous THF (72 mL) was added dropwise n-BuLi (46 mL, 91 mmol) at −78° C. The mixture was stirred at this temperature for 10 min. Aqueous HCl (1 M, 30 mL) was added to quench the reaction. The mixture was extracted with EtOAc, washed with brine, dried over sodium sulfate and concentrated to give compound 10F (3.5 g, 70%). This crude product was used directly in the next step without further purification.

Step 6.

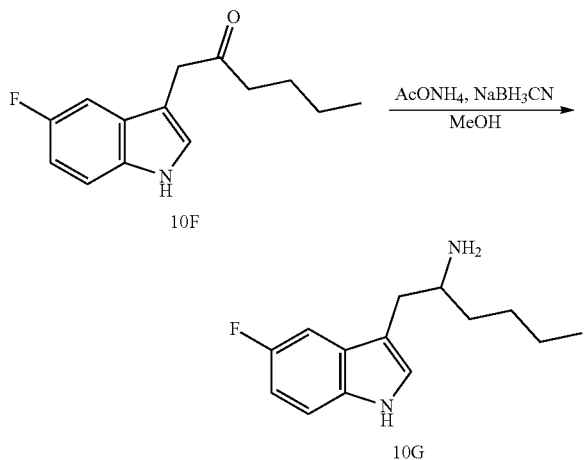

To a solution of AcONH$_4$ (46 g, 0.6 mol) and NaBH$_3$CN (9.5 g, 0.15 mol) in MeOH (140 mL) and THF (30 mL) was added compound 10F (3.5 g, 15 mmol). The mixture was stirred at room temperature for 20 h. MeOH and THF were removed in vacuo and sat. NaHCO$_3$ was added to the residue. The solution was extracted with EtOAc (100 mL×2). The organic phase was washed with brine, dried over sodium sulfate and concentrated to give compound 10G (4.0 g, 100%) as brown oil. This crude product was used directly in the next step without further purification.

Step 7.

To a solution of compound 10C (1.6 g, 6.6 mmol) in dichloromethane (6.4 mL) and THF (16 mL) was added Mukaiyama reagent (2.2 g, 8.6 mmol) and DIPEA (1.6 g, 6.6 mmol). The resultant mixture was stirred for 10 min. Compound 10G (1.6 g, 6.8 mmol) was added and the mixture was stirred at 40° C. for 2 h. The resulting precipitate was filtered off and the filtrate was concentrated in vacuo. The residue was dissolved in ethyl acetate (30 mL), washed with water (10 mL) and brine (10 mL), dried over sodium sulfate and concentrated. The residue was purified by preparative HPLC (Shimadzu LC-8A Preparative HPLC, Luna(2) C18 column, 25%-55% acetonitrile in 10 mM aqueous NH$_4$HCO$_3$ over 20 min at 80 mL/min) to give Example 10 (300 mg, 9.8%) as a white solid. $^1$H NMR (400 MHz, CDCl$_3$) δ 8.38 (s, 1H), 7.74 (s, 1H), 7.16 (t, J=4.4 Hz, 1H), 7.01 (s, 1H), 6.81-6.86 (m, 1H), 5.80 (d, J=8.8 Hz, 1H), 4.33 (d, J=5.2 Hz, 1H), 3.63 (s, 4H), 3.05 (t, J=6.4 Hz, 2H), 2.89-2.94 (m, 2H), 2.64-2.66 (m, 2H), 2.43 (s, 4H), 1.55-1.58 (m, 1H), 1.42-1.44 (m, 1H), 1.22-1.31 (m, 4H), 0.80 (t, J=6.8 Hz, 3H).

Example 11: N-(1-(1H-Indol-3-yl)hexan-2-yl)-2-morpholinothiazole-5-carboxamide

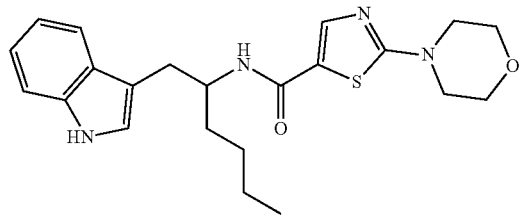 [SMILES: CCCCC(Cc1c[nH]c2ccccc12)NC(=O)c1cnc(N2CCOCC2)s1]

To a mixture of compound 3A (200 mg, 0.49 mmol) and DIPEA (171 μL, 0.98 mmol) in THF (2 mL) was added morpholine (42 μL, 0.49 mmol). The mixture was stirred for 1.5 h at 170° C. in a sealed Q-tube pressure reactor. Additional morpholine (42 μL, 0.49 mmol) was added and the mixture was heated for 0.5 h at 170° C. in a sealed Q-tube pressure reactor. The mixture was concentrated and the residue was purified by column chromatography (0-5% MeOH/DCM) to give compound Example 11 (148 mg, 73%). $^1$H NMR (400 MHz, CDCl$_3$) δ 8.08 (br s, 1H), 7.64 (d, J=7.5 Hz, 1H), 7.39 (s, 1H), 7.37 (d, J=8 Hz, 1H), 7.19 (dd, J=7.5 Hz, 1H), 7.12 (dd, J=7.5 Hz, 1H), 7.05 (d, J=2 Hz, 1H), 5.57 (d, J=8 Hz, 1H), 4.39-4.42 (m, 1H), 3.80 (t, J=4.5 Hz, 4H), 3.51 (t, J=4.5 Hz, 4H), 3.06 (dd, J=14.5, 5.5 Hz, 1H), 3.01 (dd, J=14.5, 5.5 Hz, 1H), 1.26-1.64 (m, 6H), 0.87 (t, J=7 Hz, 3H). ESMS+: 413.6 [M+1].

Examples 12-26 may be prepared according to the methods described above.

Example 27: (S)—N-(1-(1H-Indol-3-yl)hexan-2-yl)-2-(4-methylpiperazin-1-yl)thiazole-5-carboxamide and Example 28: (R)—N-(1-(1H-Indol-3-yl)hexan-2-yl)-2-(4-methylpiperazin-1-yl)thiazole-5-carboxamide

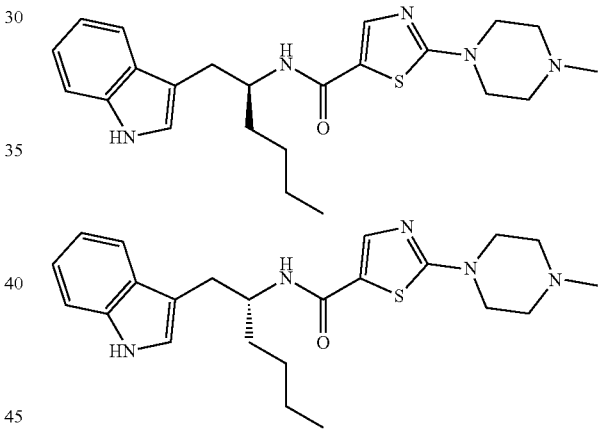

Enantiomers were separated on a THAR 80 preparative SFC using a Chiralpak AD-H column (250×30 mm; 5 μM id). The racemate was dissolved in methanol (50 mg/mL) and 45 mg of racemate was loaded per injection. The separation was achieved using a mobile phase of 40% 2-propanol (additive: 0.05% NH$_3$H$_2$O) in CO$_2$ at a flow rate of 70 g/min and a system back pressure of 100 bar. The column temperature was maintained at 40° C. and peaks were detected at 220 nm. Total cycle time was 6 minutes. Example 27 ((S)—N-(1-(1H-Indol-3-yl)hexan-2-yl)-2-(4-methylpiperazin-1-yl)thiazole-5-carboxamide): LCMS (Xtimate C18, 2.1×30 mm, 3 μM id): Peak 1 RT: 2.036 (100%) MS: 426.2; Optical rotation (Dichrom Polaraizer, 589 nM) −0.143 (sd=0.0004); Chiral purity check (OJ-H, 40% MeOH (0.05% DEA)) Peak 1 RT: 3.61 (99.87%), Peak 2 RT: 5.3 (0.13%). Example 28 ((R)—N-(1-(1H-Indol-3-yl)hexan-2-yl)-2-(4-methylpiperazin-1-yl)thiazole-5-carboxamide): LCMS (Xtimate C18, 2.1×30 mm, 3 μM id): Peak 1RT: 2.035 (98.77%) MS: 426.2. Peak 2RT: 2.373 (1.23%) MS: 427.2; Optical rotation (Dichrom Polaraizer, 589 nM)+0.160

(sd=0.0003); Chiral purity check (OJ-H, 40% MeOH (0.05% DEA)) Peak 1 RT: 3.6 (0.18%), Peak 2 RT: 5.23 (99.82%).

Biological Example 1: In-Vitro Fluorescence Polarization Assay with Alpha-Synuclein Peptide Fragment (4F)

The fluorescence polarization assay tests the ability of compounds to inhibit the self-aggregation of α-synuclein peptide fragments. Peptides were incubated for 60 min at room temperature in the presence or absence of test compounds (compound concentrations were 33.3 to 0.3 μM). Samples were read on a BMG Pherastar plate reader in fluorescence polarization mode using excitation at 485 nm and emission at 520 nm. Data was analyzed using a four-parameter logistic fit (XLFit, IDBS Software). Peptide 4F (CTGFVKKDQLGK (SEQ ID NO: 1)) was prepared by American Peptide. Fresh peptide samples were reconstituted in purified water at 5 mM and diluted into 50 mM HEPES pH 7.4 with 50 mM NaCl to 100 nM final concentration. Solid compounds were dissolved in DMSO (10 mM), and then diluted in buffer.

Data for compounds tested are presented in Table 1. Comparative compounds A and B were also tested.

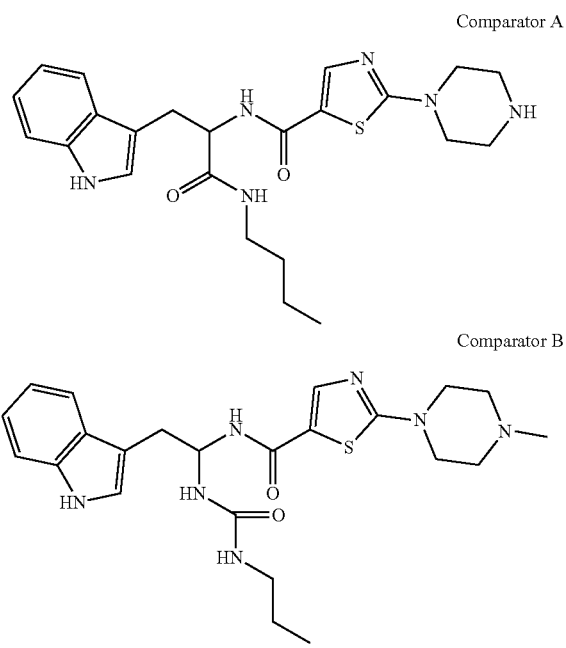

Comparator A

Comparator B

TABLE 1

| Ex. | IC$_{50}$ (μM)* |
|---|---|
| Comp. A | >30$^§$ |
| Comp. B | 6.35 |
| 1 | 3.33 ± 1.9$^¥$ |
| 2 | 3.55 |
| 3 | 0.27 |
| 4 | 5.9 |
| 5 | 1.3 |
| 6 | 0.39 |
| 7 | 0.37 |
| 8 | 0.77 |
| 9 | 8.5 |

TABLE 1-continued

| Ex. | IC$_{50}$ (μM)* |
|---|---|
| 27 | 0.4 ± 0.3$^§$ |
| 28 | 0.7 ± 0.4$^§$ |

*n = 1 unless otherwise noted
$^§$n = 2
$^¥$n = 3 ± SEM

Biological Example 2: In Vivo Pharmacokinetic Assays

The pharmacokinetics and brain distribution of the compounds described herein was determined in male C57BL/6 mice following single intravenous or oral dose administration. A group of 54 male mice were divided into two groups of 27 mice. Animals in Group 1 (i.v.) and Group 2 (p.o.) were dosed with test compounds at 10 mg/kg (i.v.) or 2 mg/kg (p.o.). Blood samples were collected pre-dose and at 0.08, 0.25, 0.5, 1, 2, 4, 8, and 24 h post-dose (i.v.), and pre-dose, and at 0.25, 0.5, 1, 2, 4, 6, 8 and 24 h post-dose (p.o.). Blood was collected from sets of three mice at each time point in labeled microcentrifuge tubes containing K$_2$EDTA as anticoagulant. Plasma samples were separated by centrifugation of whole blood and stored below −70° C. until bioanalysis. After collecting blood samples, mice were humanely euthanized by CO$_2$ asphyxiation and brain was collected at the same time points. Following collection, the brain samples were washed in ice-cold phosphate buffer saline (pH 7.4), gently dried on filter paper, weighed and placed in polypropylene tubes. Further brain samples were homogenized using phosphate buffer saline pH 7.4 and the total homogenate volume was thrice the brain weight. The samples were then stored below −70° C. until bioanalysis. All samples were processed for analysis by protein precipitation using acetonitrile and analyzed with fit-for-purpose LC/MS/MS method (LLOQ: 1.01 ng/mL for plasma and brain). Pharmacokinetic parameters were calculated using the non-compartmental analysis tool of Phoenix WinNonlin (Version 6.3).

Data obtained from this assay are presented in Table 2.

TABLE 2

| Ex. | Stability in SGF | Plasma Stability | Oral Bioavail-ability* | PK Clearance* (mL/min/kg) | B:P ratio* (IV/PO) |
|---|---|---|---|---|---|
| Comp. A | stable | 35% @ 60 min | NC | 71 | NC/0.05 |
| Comp. B | unstable | 89% @ 60 min | 14% | 258 | 0.1/0.08 |
| 1 | stable | 100% @ 120 min | 53% | 81 | 2.0/0.4 |
| 4 | stable | 25% @ 120 min | 100% | 95 | 0.4/0.1 |
| 5 | stable | 100% @ 120 min | 79% | 24 | 0.18/0.05 |
| 10 | ND | ND | 13% | 75** | 0.8**/0.15 |
| 27 | ND | ND | 57% | 37 | 1.4/0.3 |
| 28 | ND | ND | 14% | 69 | 2.1/0.4 |

*at 10 mg/kg
**at 2 mg/kg
NC = No compound detected (below detection limit)
ND = Not determined Biological Example 3: NMR Assay for Effect of Test Compounds on Alpha-Synuclein Interaction with Lipid Membranes To measure the interaction of test compounds with full-length ASYN in the presence of lipid membranes, an NMR assay was conducted. NMR measurements were made in 20 mM Phosphate, pH=7.4, 100 mM NaCl on Varian Direct Drive 600 MHz and Varian Inova 800 MHz spectrometers with 10% D20 as lock solvent. Spectra were processed using NMRPipe (see F. Delaglio, S. Grzesiek, G. W. Vuister, G. Zhu, J. Pfeifer, A. Bax, *J Biomol NMR* 1995, 6, 277-293). α-Synuclein was used at 0.12 mM while 1-palmitoyl-2-oleoyl-sn-glycero-3-phosphoglycerol (POPG)-liposomes were added at 0.8 mg/ml where present. All $^1H$-$^{15}N$ correlation spectra were recorded with a SOFAST pulse sequence (see P. Schanda, E. Kupce, B. Brutscher, *J Biomol NMR* 2005, 33, 199-211). Resonance assignment at near physiological conditions was readily available from a previous publication (BMRB ID 16300; see J. N. Rao, Y. E. Kim, L. S. Park, T. S. Ulmer, *J Mol Biol* 2009, 390, 516-529). For ligand titration, Example 1 was added stepwise to the liposome/ASYN mixture. $^{15}N$-$^1H$ correlation spectra were recorded for each step and the signal intensities were referenced to the free form of ASYN while accounting for dilution effects. To reduce noise in the available data, the intensity ratio for several amide positions of ASYN was averaged for two regions chosen to correspond to the SL1 and SL2 binding modes observed previously (see C. R. Bodner, A. S. Maltsev, C. M. Dobson, A. Bax, *Biochemistry* 2010, 49, 862-871).

As shown in FIG. 1, the heteronuclear single quantum coherence (HSQC) spectroscopy signal intensity for ASYN is attenuated when ASYN is embedded in lipid membranes. This lipid-induced attenuation of the HSQC signal was reversed by Example 1, thus demonstrating the ability of the test compound to disrupt the association of ASYN with lipid membrane. FIG. 1A shows the signal attenuation as function of ASYN residues in the presence of POPG liposomes. The Y axis (I/Io) is the ratio of the HSQC spectroscopy signal intensities for ASYN in the presence (I) or absence (Io) of lipid membranes. In FIG. 1B, the average I/Io ratio of ASYN residues 3-23 was plotted as a function of the concentration of Example 1 added. This plot shows that Example 1 reversed the interaction of ASYN with 1-palmitoyl-2-oleoyl-sn-glycero-3-phosphoglycerol (POPG) (0.8 mg/mL) liposomes in a concentration-dependent manner. Similar results were obtained when ASYN residues 66-76 were analyzed.

Biological Example 4: Effect of Test Compounds on Annular Oligomers in Lipid Membranes Electron microscopy was used to directly visualize the effect of test compounds on the formation of ASYN oligomers in lipid membranes. Formvar grids with the lipid monolayer were counterstained with a saturated uranyl acetate solution in 50% ETOH for 25 minutes. The grids were then floated on a droplet of 2% bismuth subnitrate for 10 min, and again carefully rinsed with double distilled water three times and allowed to completely dry. Grids were imaged using a Zeiss EM10 transmission electron microscope Electron Microscope. From each sample grid, 5-10 electron micrographs at 10,000× magnification and 5-10 images at 40,000× were obtained. The best negatives were scanned and analyzed with the ImageJ 1.43 program to estimate the numbers of annular oligomers per higher power field (100×100 nm) (Rasband, W. S., ImageJ, U. S. National Institutes of Health, Bethesda, Md., USA, http://imagej.nih.gov/ij/, 1997-2014).

In this study, Example 1 was found to dramatically reduce the accumulation of annular, ring-like, oligomeric forms of ASYN in a lipid membrane, while small non-annular aggregates were still observed. FIG. 2 is a graph that reflects the quantification of the electron microscopic images. Example 1 reduced the number of annular ASYN oligomers detected on the Formvar grids at concentrations as low as 10 nM (means±SEM for 20 measurements). Example 1 achieved these effects at sub-stoichiometric concentrations relative to ASYN. These findings were consistent with the molecular dynamic modeling showing that Example 1 stabilizes conformations of ASYN less likely to form ring-like oligomers in lipid membranes.

These results suggest that Example 1 interacts with oligomeric and lipid-bound forms of ASYN in a way that reduces the affinity of ASYN oligomers for the lipid membrane. Example 1 was able to interfere with ASYN oligomerization, the binding of ASYN to lipid membranes, and the formation of annular ring-like oligomers ("pores") in these membranes. These results also suggest that Example 1 alters the aggregation of ASYN and prevents the formation of specific oligomeric structures believed to contribute to the neurotoxicity of misfolded, oligomerized ASYN in Parkinson's disease.

Biological Example 5: Effect of Test Compounds on Alpha-Synuclein in Cells

The effect of Example 1 on accumulation of ASYN in B103 neuroblastoma cells overexpressing human ASYN was studied. A lentiviral expression system was used to express GFP-tagged ASYN in these cells. Forty-eight hours after expression was initiated, vehicle or Example 1 (0.1 or 1.0 μM) was added for an additional 24 hours. The amount of accumulated GFP-ASYN was then visualized. As shown in FIG. 3, Example 1 reduced the intensity of GFP florescence in these cells at 1.0 μM (*$p<0.05$ vs. vehicle control group). Example 1 was therefore found to reduce concentrations of ASYN-GFP in ASYN-overexpressing cells.

Biological Example 6: In Vivo Efficacy Studies

Parkinson's disease (PD) is characterized by aberrant accumulation of oligomeric forms of alpha-synuclein (ASYN). It is hypothesized that these toxic forms of ASYN contribute to the neuronal dysfunction and cell death observed in PD and other synucleinopathies, in part, though the formation of pore-like structures in cell membranes. The compounds described herein were designed to ameliorate PD-related symptoms and pathology by selectively blocking the formation and accumulation of these toxic species of ASYN.

A) Transgenic Mouse Model of Parkinson's Disease

Example 1 was evaluated in a transgenic mouse model of PD overexpressing human wild-type ASYN under the Thy-1 promoter (also referred to as the Line 61 ASYN transgenic mouse), by administering Example 1 a Tant 0, 1, or 5 mg/kg (i.p.) once daily (five days per week) for three months and then assessing PD-relevant sensorimotor performance, biochemical alterations, and neuropathological changes in ASYN and related proteins.

The Round Beam Task was used to assess sensorimotor impairments, using number of slips as the primary outcome measure (FIG. 4). To confirm the viability of the transgenic mouse model, ASYN transgenic and non-transgenic mice were tested, and the number of slips for vehicle-treated transgenic subjects was statistically significantly higher than in the vehicle-treated non-transgenic control group (****$p<0.0001$). Transgenic mice treated with Example 1 at both test doses had statistically significantly reductions in slips compared to vehicle-treated transgenic mice (#p<0.05 and ##p<0.01 vs. vehicle-treated ASYN transgenic mice).

Figure 5:
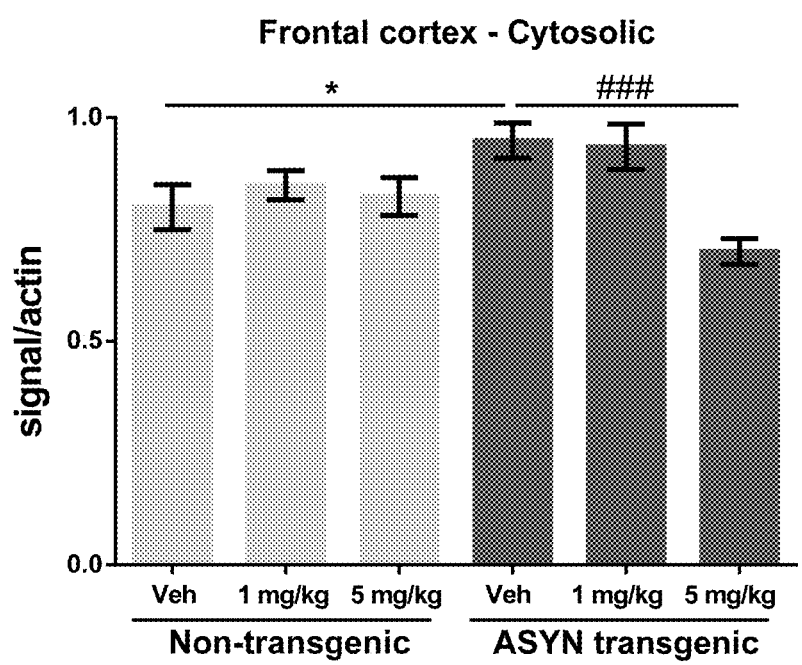
FIG. 5 shows the results of the Biological Example 6A dot blot analysis of cerebral and hippocampal brain homogenates using A11 antibody.

Western Blot analysis of cerebral cortical and hippocampal brain homogenates revealed statistically significant reductions in transgenic ASYN protein levels. Biochemical evaluations of oligomeric proteins using A11 antibody dot blot methods (including ASYN) in cortical homogenates were performed. The transgenic mouse model was verified, as A11 antibody dot blot evaluation of oligomers in cortical homogenates showed a statistically significant increase in A11 immunostaining in the cytosolic fraction of the frontal cortex in vehicle-treated ASYN transgenic mice relative to vehicle-treated non-transgenic control mice (FIG. 5; *p<0.05). Treatment with Example 1 (5 mg/kg) yielded a statistically significant decrease in oligomers in the cytosolic fraction from the frontal cortex region of mice relative to vehicle-treated ASYN transgenic mice (FIG. 5; ####p<0.001).

B) Line 61 ASYN Transgenic Mouse Models

Figure 6:
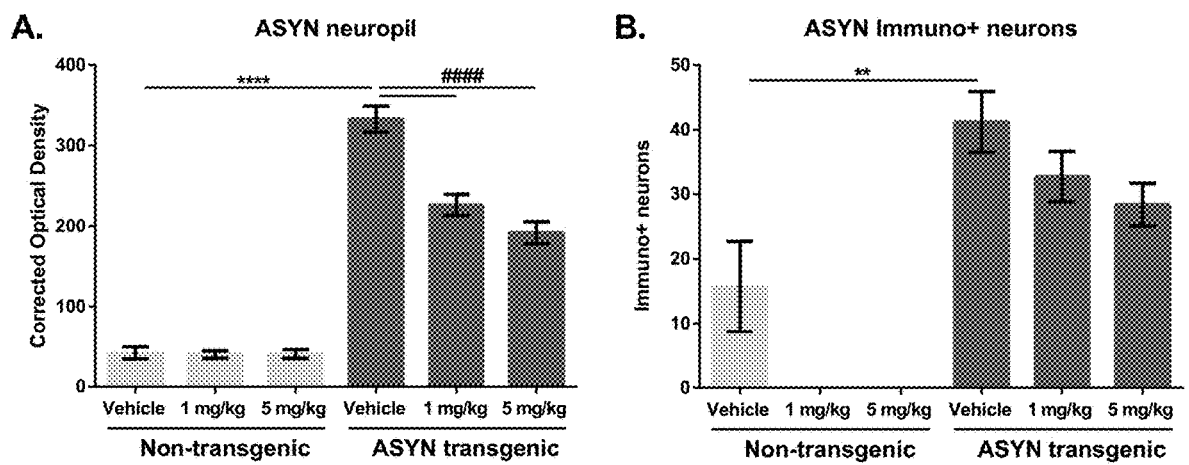
FIG. 6 shows the results of Biological Example 6B and the effects of Example 1 on ASYN immunolabeling in cortical neuropil and neuronal cell bodies in Line 61 ASYN transgenic mice.
Figure 7:
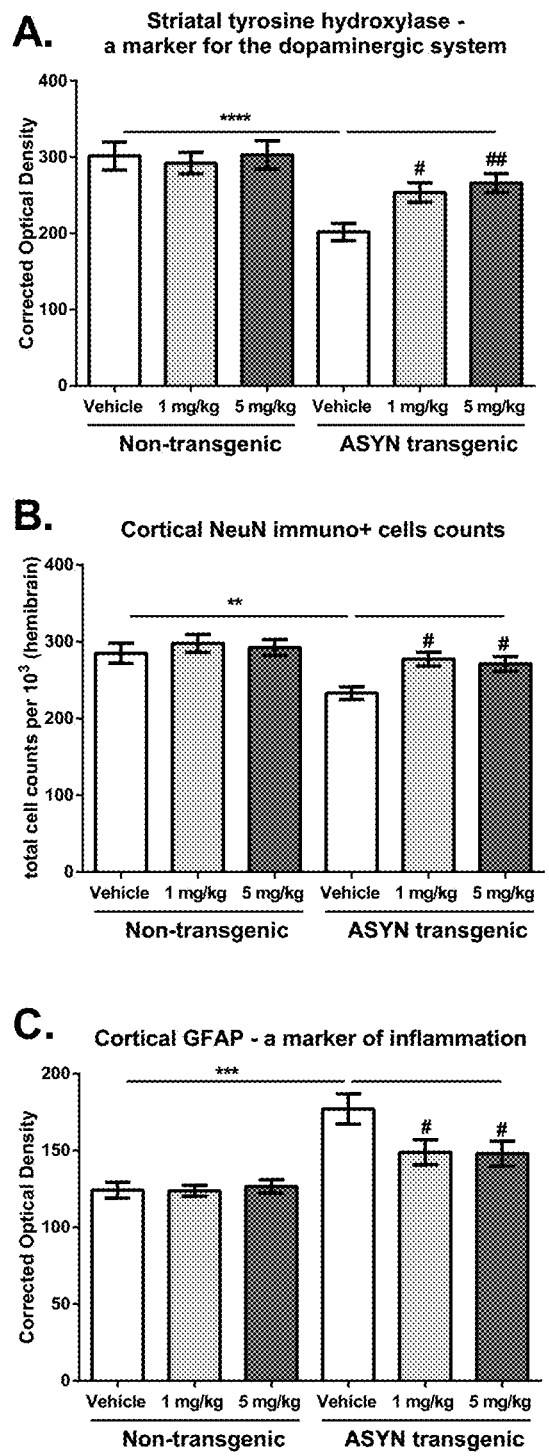
FIG. 7 shows the results of Biological Example 6B and the effects of Example 1 on immunolabeling of neurodegeneration-related markers including tyrosine hydroxylase (FIG. 7A), NeuN (FIG. 7B), and glial fibrillary acidic protein (GFAP.

Previous immunolabeling studies by Masliah and colleagues have demonstrated statistically significant increases in ASYN immunolabeling in cortical neuropil in the Line 61 ASYN transgenic mouse (Masliah E. et al., *Science*, 2000, 287(5456):1265-9). These neuropathological findings were reconfirmed in the current study using the methods described by Masliah and colleagues. Example 1 administration (1 and 5 mg/kg dosing) produced statistically significant decreases in ASYN levels as determined by effects on ASYN immunolabeling (FIGS. 6 and 7). There was a statistically significant increase in ASYN immunolabeling with the Millipore anti-alpha-synuclein antibody in the cortical neuropil (**p<0.0001) (FIG. 6A) and in neuronal cell bodies of ASYN transgenic mice (p<0.01) (FIG. 6B) relative to non-transgenic/vehicle controls. Example 1 (1 and 5 mg/kg) administration produced statistically significant decreases in alpha-synuclein immunolabeling in cortical neuropil (FIG. 6A) (#####p<0.0001 vs. vehicle-treated ASYN transgenic mice), and a non-statistically significant decrease in the number of ASYN immunolabeled neuron cell bodies at 5 mg/kg (FIG. 6B).

Moreover, normalization of neurodegeneration-related markers including tyrosine hydroxylase, NeuN, and GFAP were observed.

Figure 8:
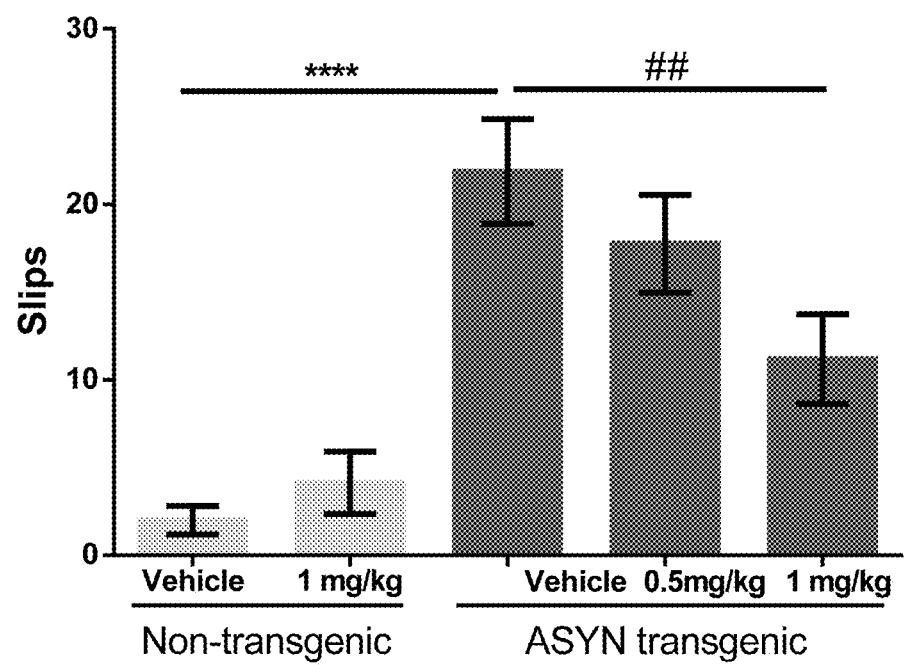
FIG. 8 shows the results of Biological Example 6B and the effects of Example 1 on sensorimotor impairment in Line 61 ASYN transgenic mice using the Round Beam Motor Performance assay.

As shown in FIG. 8, the effect of Example 1 at 0.5 mg/kg and 1 mg/kg on sensorimotor impairment in Line 61 ASYN transgenic mice was studied, using the Round Beam Motor Performance assay described above. A statistically significant increase in the number of slips was observed in vehicle-treated ASYN transgenic control mice as compared to vehicle-treated non-transgenic control subjects (****p<0.0001). At 1 mg/kg, Example 1 treatment produced a statistically significant improvement (decreased slips) in ASYN transgenic mice relative to vehicle-treated ASYN transgenic mice (##p<0.01). At 0.5 mg/kg, Example 1 produced a non-statistically significant decrease in slips.

Together, these results demonstrate that Example 1 significantly improves sensorimotor, biochemical, and neuropathological outcomes in a transgenic mouse model. These findings confirmed that administration of Example 1 produces improvements in behavioral, biochemical, and neuropathological measures in a transgenic mouse model of Parkinson's disease/Dementia with Lewy bodies (PD/DLB).

Biological Example 7: Development of Biological Markers

A) Fecal Boli Counts

In efforts directed toward development of translatable functional and biochemical biomarkers, additional evaluations were conducted, including an assessment of fecal boli counts produced in a novel environment and post-mortem cardiac levels of ASYN.

Chronic constipation in Parkinson's patients has a prevalence of 50-80%, and may precede diagnosis by 20+ years (Awad, R. A. *World J. Gastroenterol.* 2011, 17(46), 5035-5048; Kim, J. S. et al., *J. Neurol. Sci.* 2011, 310 (1-2), 144-151). Associated symptoms include decreased transit times and EMG abnormalities (sphincter, rectoanal inhibitory reflexes), and are accompanied by key pathological findings including Lewy bodies in parasympathetic nuclei and nerves, and decreased dopaminergic neurons. This bowel dysfunction is compounded by decreased activity levels, changes in diet (food and water), and effects of Parkinson's medications.

Figure 9:
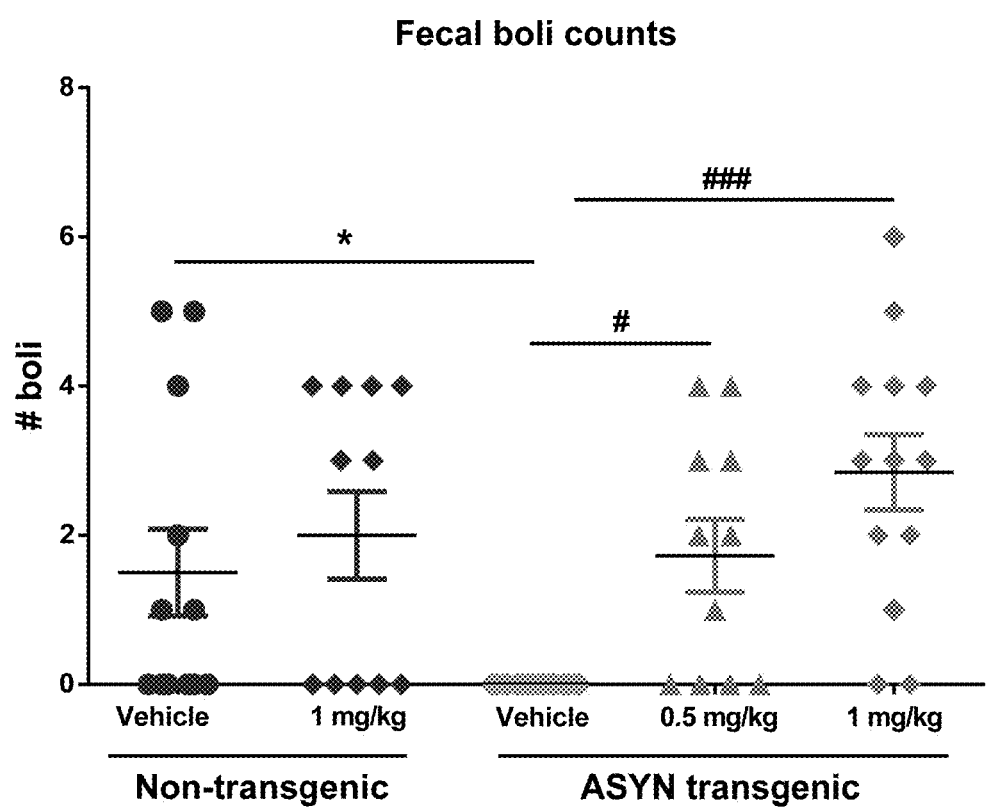
FIG. 9 shows the results of Biological Example 7A and the effects of Example 1 on fecal boli counts in Line 61 ASYN transgenic mice.

An earlier published study included a report that Line 61 ASYN transgenic mice have decreased colonic motility, fecal output, and weight (Wang, L. et al. *Neurogastroenterol. Motil.* 2012, 24(9), e425-436). For the present study, an assessment of fecal boli counts was conducted in conjunction with a spontaneous locomotor activity test session. At the conclusion of a five-minute test session, the experimenter counted the number of fecal boli present in the test chamber, and the results are presented in FIG. 9. Vehicle-treated ASYN transgenic mice had statistically significant reductions in fecal boli produced in a novel environment relative to vehicle-treated non-transgenic control mice (*p<0.05). Example 1 had no effect on number of boli produced in non-transgenic mice, but restored function in ASYN transgenic mice at 0.5 mg/kg (#p<0.05 vs. vehicle-treated ASYN transgenic mice) and 1 mg/kg (####p<0.001 vs. vehicle-treated ASYN transgenic mice).

B) Cardiac Function

Figure 10:
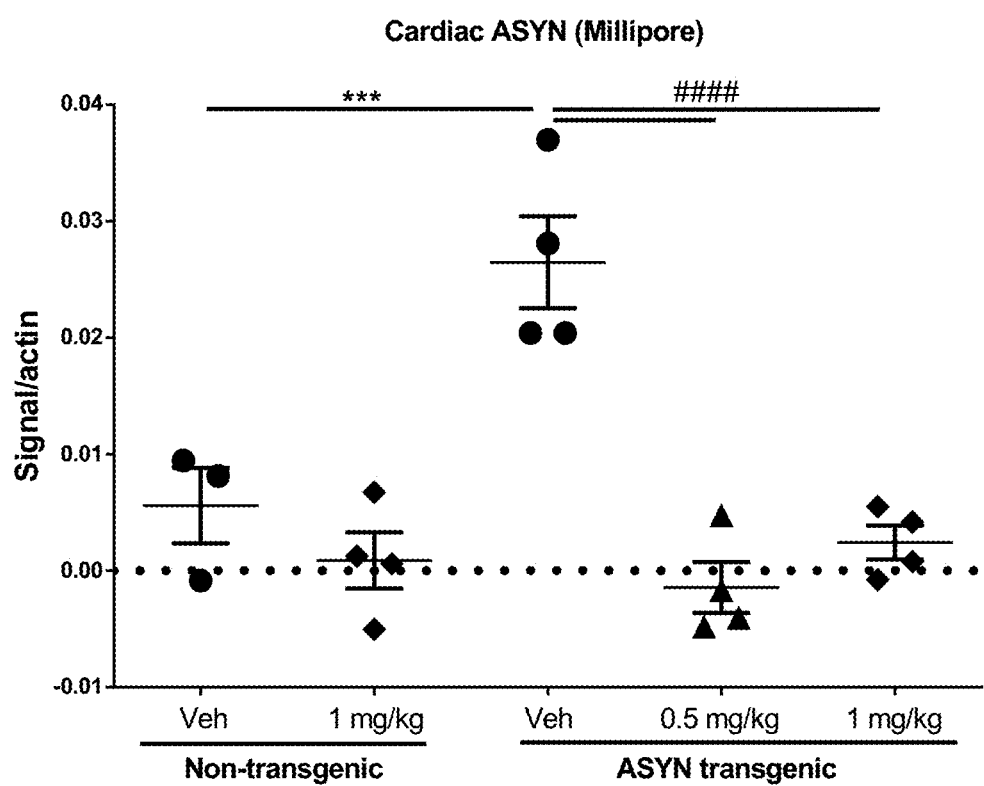
FIG. 10 shows the results of Biological Example 7B and the effects of Example 1 on cardiac levels of ASYN in Line 61 ASYN transgenic mice.

Like bowel dysfunction, alterations in cardiac biochemistry and function may precede Parkinson's disease diagnosis by 20 years or more. Well-characterized functional alterations in PD patients include altered heart rate variability and orthostatic hypotension (Kaufmann, H. et al., *Handbook Clin. Neurol.* 2013, 117, 259-278; Jain, S. et al., *Neurobiol. Dis.* 2012, 46(3), 572-580; Senard, J. M. et al., *Rev. Neurol.* (Paris) 2010, 166(10), 779-784; Post, K. K. et al., *Parkinsonism Relat. Disord.* 2008, 14(7), 524-531). These functional changes are accompanied by pathological findings of loss of myocardial noradrenergic innervation and the presence of ASYN aggregates in cardiac autonomic nerves (Jellinger, K. A., *J. Neurol. Sci.* 2011, 310 (1-2), 107-111). Previous characterizations of cardiac function and biochemistry in Line 61 ASYN transgenic mice have demonstrated the presence of hASYN in the ventricular and atrial walls of the heart localized within noradrenergic fibers (Fleming, S. M., *J. Parkinsons Dis.* 2011, 1(4), 321-327). For the present study, post-mortem Western blot evaluations of cardiac ASYN by Western blot analysis were performed to confirm the presence in ASYN transgenic cardiac tissue and to evaluate the effects of Example 1 on transgenic cardiac levels of ASYN (FIG. 10). There was a statistically significant increase in detected cardiac levels of ASYN in vehicle-treated ASYN transgenic mice relative to vehicle-treated non-transgenic control mice (***p<0.001). There were statistically significant normalizations of ASYN levels in ASYN transgenic mice treated with either 0.5 or 1 mg/kg of Example 1 relative to vehicle-treated ASYN transgenic mice (####p<0.0001).

C) Retinal Imaging

Abnormal accumulation of a neuronal protein alpha-synuclein (ASYN) has been hypothesized to underlie neuronal cell death and synaptic dysfunctional in Parkinson's disease (PD) and Dementia with Lewy Bodies (DLB). Compounds that selectively interfere with alpha-synuclein protein-folding dynamics and prevent the formation of propagating dimers have been developed and further evaluated in animal models. Alterations in visual function are present in some Parkinson's patients (Botha, H. et al., *Parkinsonism Relat. Disord.* 2012, 18(6), 742-747; Bodis-Wollner, I. et al., *Behav. Neurosci.* 2013, 127(2), 139-150; Bodis-Wollner, I., *Parkinsonism Relat. Disord.* 2013, 19(1), 1-14; Javaid, M. A. et al., *Parkinsonism Relat. Disord.* 2012, 18 (Suppl. 1), S100-3) and recent reports have presented potential pathological changes in PD retinae. Optical coherence tomography (OCT) studies have demonstrated a decreased retinal nerve fiber layer in Parkinson's patients (Yu, J. G. et al., *PLoS One* 2014, 9(1), e85718). Post-mortem assessments have revealed ASYN deposits in PD retina (Bodis-Wollner, I. et al., *Ann. Neurol.* 2014, 75(6), 964-6).

The feasibility of repeated longitudinal retinal imaging evaluations of e-GFP-ASYN in the PDNG78 transgenic mouse model of DLB/PD was demonstrated previously as a method to evaluate and track the progression of neurodegenerative changes in animal models of Parkinson's disease (Rockenstein et al., "Retinal scanning evaluations of alpha-synuclein-eGFP deposition in a transgenic mouse model of PD/DLB," Society for Neurosciences, Annual Meeting, 2013, Abstract No. 329.06). Progressive pathological features in the PDNG78 retina were shown to mirror CNS pathology, thereby providing a means to non-invasively and repeatedly evaluate potential therapeutic interventions in a transgenic mouse model of PD/DLB.

This study was conducted to determine the effect of Example 1 (3 months i.p. administration at 0 & 5 mg/kg) on the presence and progression of alpha-synuclein (ASYN) retinal pathology in a longitudinal retinal imaging study in a transgenic mouse model of Parkinson's disease/Dementia with Lewy Bodies (PD/DLB). The transgenic mice subjects overexpress fused alpha-synuclein-GFP (green fluorescent protein) under the PDGF-beta promoter and are commonly referred to as PDNG78 transgenic mice (Rockenstein, E. et al., *J. Neurosci. Res.* 2005, 80, 247-259). The PDNG78 transgenic mouse expresses fused ASYN-GFP at levels 2-5 fold greater levels than non-transgenic control mice. The CNS expression levels of ASYN are highest in the limbic system, including the neocortex and hippocampal regions, of PDNG78 transgenic mice. Cellular distributions of ASYN-GFP mirror synucleinopathy-relevant features including accumulations in neuronal cell bodies, diffuse staining of the neuropil, synaptic punctate staining, and perivascular deposits.

Figure 11:
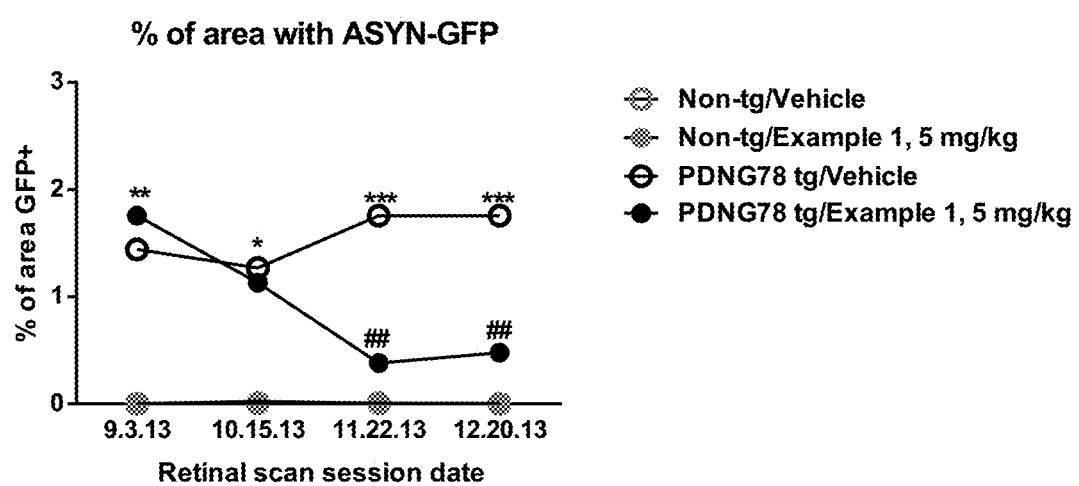
FIG. 11 shows the results of Biological Example 7C and the effects of Example 1 on percentage of image areas with ASYN-GFP in the retinae of PDNG78 transgenic mice.

A total of four imaging sessions were conducted, including a baseline prior to starting treatments and three subsequent imaging sessions at approximately one-month intervals. Analysis of retinal images for percentage of image with ASYN-GFP (FIG. 11) showed statistically significant increases in the percentage of image areas with ASYN-GFP in the retinae of transgenic mice at baseline prior to commencement of treatments (**p<0.01 vs. vehicle-treated non-transgenic mice) and for each subsequent scan (*p<0.05 and ***p<0.001 vs. vehicle-treated non-transgenic mice). The percentage of ASYN-GFP positive area decreased in transgenic mice treated with Example 1 (5 mg/kg) after approximately 60 days of treatment and persisting through the 90 day imaging time point (###p<0.001 vs. vehicle-treated ASYN transgenic mice).

Figure 12:
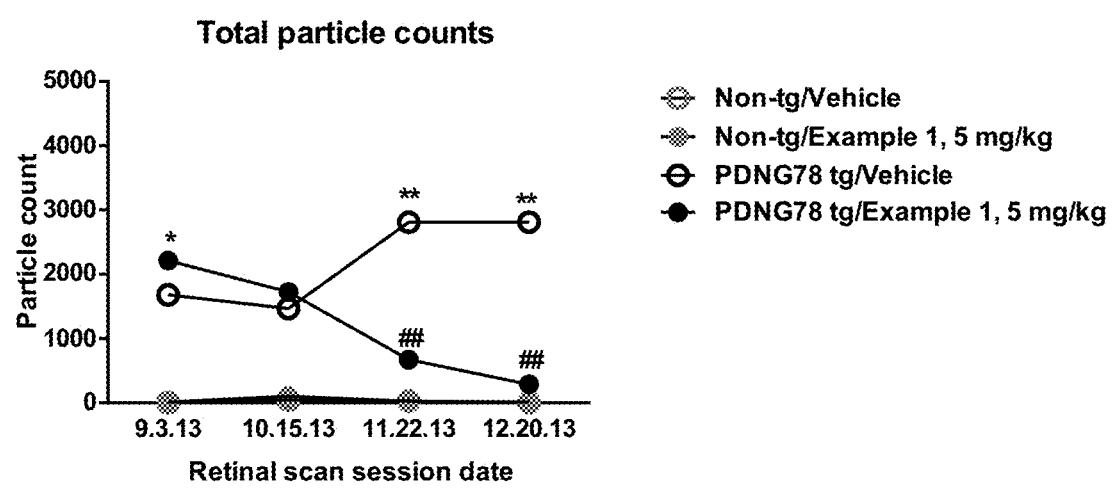
FIG. 12 shows the results of Biological Example 7C and the effects of Example 1 on perivascular and nerve terminal GFP labeling in PDNG78 transgenic mice.

Analysis of ASYN-GFP positive particle counts (FIG. 12) revealed increased and persistent perivascular and nerve terminal green fluorescent protein (GFP) labeling in transgenic, but not non-transgenic mice. There were statistically significant increases in total ASYN-GFP particle counts in the retinae of transgenic mice at baseline prior to commencement of treatments (*p<0.05 vs. vehicle-treated non-transgenic mice) and for scans starting at approximately 60 days of treatments (**p<0.01 vs. vehicle-treated non-transgenic mice). The number of ASYN-GFP positive particles was decreased in ASYN transgenic mice treated with Example 1 (5 mg/kg) after approximately 60 days of treatment and persisting through the 90 day imaging time point (##p<0.01 vs. vehicle-treated ASYN transgenic mice).

Findings from this study demonstrate that administration of Example 1 (5 mg/kg per day; for 3 months) produces beneficial changes in ASYN retinal pathology of transgenic mice overexpressing ASYN as a model of PD/DLB. These data also provide additional evidence measure of beneficial effects of Example 1 by a potentially translatable imaging method.

---

---

The invention claimed is:

1. A compound of Formula (I):

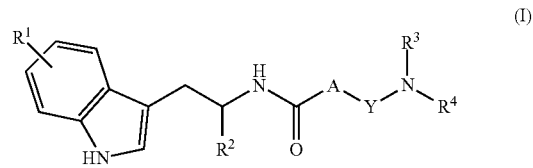

wherein
R$^1$ is H, halo, C$_{1-4}$alkyl, or —CF$_3$;
R$^2$ is —CF$_3$ or C$_{1-4}$alkyl unsubstituted or substituted with halo or —CF$_3$;
A is a 5-membered heteroaryl ring with two or three heteroatom ring atoms selected from the group consisting of N, O, and S, and wherein the 5-membered heteroaryl ring is attached to

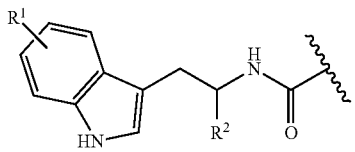

and Y via two non-adjacent carbon ring atoms;

Y is absent or is $C_{1-4}$alkylene;

where when Y is absent, $R^3$ and $R^4$ taken together with the nitrogen to which they are attached form a monocyclic heterocycloalkyl ring, unsubstituted or substituted with $C_{1-4}$alkyl; and when Y is $C_{1-4}$alkylene, $R^3$ and $R^4$ taken together with the nitrogen to which they are attached form a monocyclic heterocycloalkyl ring, unsubstituted or substituted with $C_{1-4}$alkyl; or $R^3$ and Y taken together with the nitrogen to which $R^3$ is attached form a monocyclic heterocycloalkyl ring, and $R^4$ is H or $C_{1-4}$alkyl;

or a pharmaceutically acceptable salt thereof.

2. The compound of claim 1, or a pharmaceutically acceptable salt thereof, wherein $R^1$ is H, fluoro, chloro, bromo, methyl, ethyl, propyl, isopropyl, butyl, isobutyl, sec-butyl, or tert-butyl.

3. The compound of claim 1, or a pharmaceutically acceptable salt thereof, wherein $R^1$ is H or fluoro.

4. The compound of claim 1, or a pharmaceutically acceptable salt thereof, wherein $R^1$ is —$CF_3$, or is methyl, ethyl, propyl, isopropyl, butyl, isobutyl, sec-butyl, or tert-butyl, each unsubstituted or substituted with fluoro, chloro, bromo, or —$CF_3$.

5. The compound of claim 1, or a pharmaceutically acceptable salt thereof, wherein $R^1$ is —$CF_3$ or is $C_{1-4}$alkyl optionally substituted with halo or —$CF_3$.

6. The compound of claim 1, or a pharmaceutically acceptable salt thereof, wherein $R^1$ is $C_{3-4}$alkyl, unsubstituted or substituted with fluoro or —$CF_3$.

7. The compound of claim 1, or a pharmaceutically acceptable salt thereof, wherein $R^1$ is butyl.

8. The compound of claim 1, or a pharmaceutically acceptable salt thereof, wherein $R^2$ is propyl substituted with —$CF_3$.

9. The compound of claim 1, or a pharmaceutically acceptable salt thereof, wherein $R^1$ is in an "R" stereochemical configuration.

10. The compound of claim 1, or a pharmaceutically acceptable salt thereof, wherein $R^1$ is in an "S" stereochemical configuration.

11. The compound of claim 1, or a pharmaceutically acceptable salt thereof, wherein A is a 5-membered heteroaryl ring with two heteroatom ring atoms.

12. The compound of claim 1, or a pharmaceutically acceptable salt thereof, wherein A is a 5-membered heteroaryl ring with two non-adjacent heteroatom ring atoms.

13. The compound of claim 1, or a pharmaceutically acceptable salt thereof, wherein A is thiazole, thiadiazole, oxazole, imidazole, or triazole.

14. The compound of claim 1, or a pharmaceutically acceptable salt thereof, wherein A is thiadiazole.

15. The compound of claim 1, or a pharmaceutically acceptable salt thereof, wherein A is thiazole.

16. The compound of claim 1, or a pharmaceutically acceptable salt thereof, wherein Y is absent.

17. The compound of claim 1, or a pharmaceutically acceptable salt thereof, wherein Y is —$CH_2$—, —$CH_2CH_2$—, —$CH(CH_3)$—, —$(CH_2)_3$—, —$C(CH_3)_2$—, —$(CH_2)_4$—, —$CH((CH_2)_2CH_3)$—, —$CH(CH(CH_3)_2)$—, —$CH(CH_2CH_3)CH_2$—, —$CH(CH_3)CH(CH_3)$—, —$CH(CH_3)(CH_2)_2$—, or —$CH_2CH(CH_3)CH_2$—.

18. The compound of claim 17, or a pharmaceutically acceptable salt thereof, wherein Y is —$CH_2$—, —$CH_2CH_2$—, or —$CH(CH_3)$—.

19. The compound of claim 17, or a pharmaceutically acceptable salt thereof, wherein Y is —$CH_2CH_2$—.

20. The compound of claim 1, or a pharmaceutically acceptable salt thereof, wherein $R^3$ and $R^4$ are taken together with the nitrogen to which they are attached form a monocyclic heterocycloalkyl ring, unsubstituted or substituted with $C_{1-4}$alkyl.

21. The compound of claim 20, or a pharmaceutically acceptable salt thereof, wherein $R^3$ and $R^4$ taken together with the nitrogen to which they are attached form azetidine, pyrrolidine, piperidine, azepine, piperazine, morpholine, thiomorpholine, or 1,1-dioxo-thiomorpholine, each unsubstituted or substituted with $C_{1-4}$alkyl.

22. The compound of claim 20, or a pharmaceutically acceptable salt thereof, wherein $R^3$ and $R^4$ taken together with the nitrogen to which they are attached form pyrrolidine, unsubstituted or substituted with $C_{1-4}$alkyl.

23. The compound of claim 20, or a pharmaceutically acceptable salt thereof, wherein $R^3$ and $R^4$ taken together with the nitrogen to which they are attached form morpholine, unsubstituted or substituted with $C_{1-4}$alkyl.

24. The compound of claim 20, or a pharmaceutically acceptable salt thereof, wherein $R^3$ and $R^4$ taken together with the nitrogen to which they are attached form piperazine, unsubstituted or substituted with $C_{1-4}$alkyl.

25. The compound of claim 20, or a pharmaceutically acceptable salt thereof, wherein $R^3$ and $R^4$ taken together with the nitrogen to which they are attached form piperazine or 4-methyl-piperazine.

26. The compound of claim 1, or a pharmaceutically acceptable salt thereof, wherein Y is $C_{1-4}$alkylene, and $R^3$ and Y taken together with the nitrogen to which $R^3$ is attached form a monocyclic heterocycloalkyl ring, and $R^4$ is H or $C_{1-4}$alkyl.

27. The compound of claim 26, or a pharmaceutically acceptable salt thereof, wherein Y and $R^3$ taken together with the nitrogen to which $R^3$ is attached form pyrrolidine or piperidine.

28. The compound of claim 26, or a pharmaceutically acceptable salt thereof, wherein $R^4$ is H or methyl.

29. The compound of claim 1, or a pharmaceutically acceptable salt thereof, wherein $R^1$ is H, $R^2$ is $C_{1-4}$alkyl, A is thiazole, Y is absent or is ethylene, and $R^3$ and $R^4$ taken together with the nitrogen to which they are attached form N-methylpiperazine.

30. A compound selected from the group consisting of:

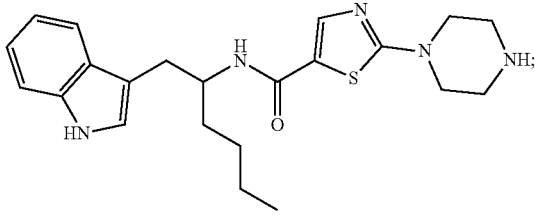

N-(1-(1H-Indol-3-yl)hexan-2-yl)-2-(piperazin-1-yl)thiazole-5-carboxamide

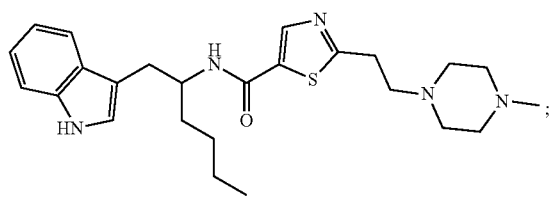

N-(1-(1H-Indol-3-yl)hexan-2-yl)-2-(2-(4-methylpiperazin-1-yl)ethyl)thiazole-5-carboxamide

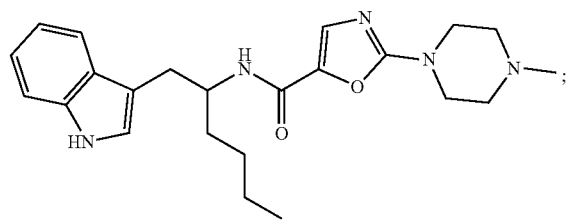

N-(1-(1H-Indol-3-yl)hexan-2-yl)-2-(4-methylpiperazin-1-yl)oxazole-5-carboxamide

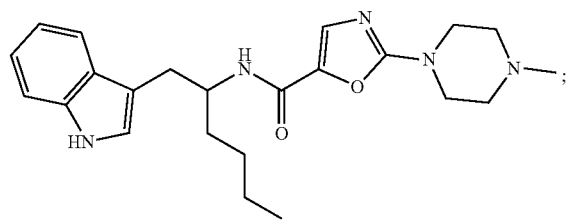

N-(1-(1H-Indol-3-yl)hexane-2-yl)-5-(4-methylpiperazin-1-yl)-1,3,4-thiadiazole-2-carboxamide

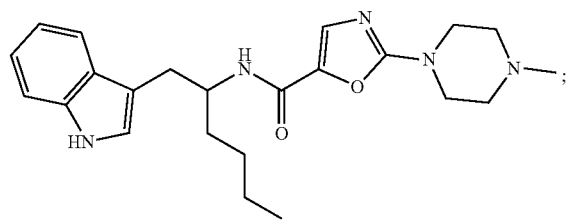

N-(1-(1H-Indol-3-yl)hexane-2-yl)-5-(4-methylpiperazin-1-yl)-4H-1,2,4-traizole-3-carboxamide

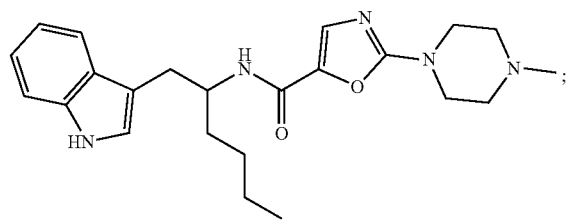

N-(1-(1H-Indol-3-yl)hexane-2-yl)-2-(4-methylpiperazin-1-yl)-1H-imidazole-5-carboxamide

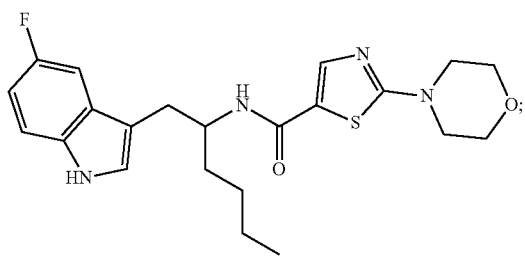

N-(1-(5-Fluoro-1H-indol-3-yl)hexan-2-yl)-2-(2-morpholinoethyl)thiazole-5-carboxamide

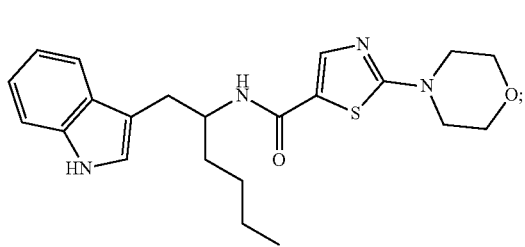

N-(1-(1H-Indol-3-yl)hexan-2-yl)-2-morpholinothiazole-5-carboxamide

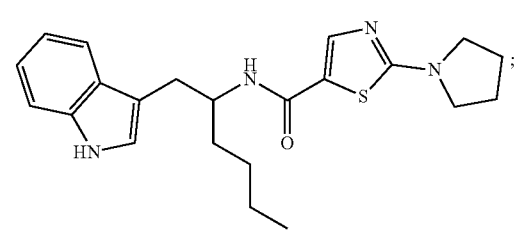

N-(1-(1H-Indol-3-yl)hexan-2-yl)-2-(pyrrolidin-1-yl)thiazole-5-carboxamide

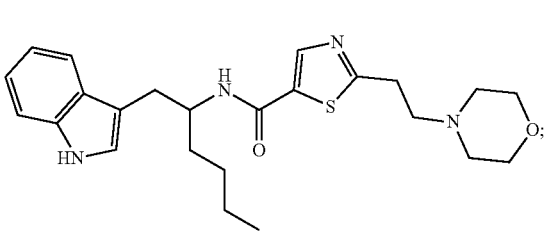

N-(1-(1H-indol-3-yl)hexan-2-yl)-2-(2-morpholinoethyl)thiazole-5-carboxamide

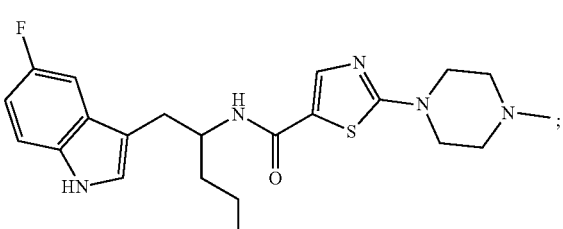

N-(1-(5-fluoro-1H-indol-3-yl)hexan-2-yl)-2-(4-methylpiperazin-1-yl)thiazole-5-carboxamide -continued

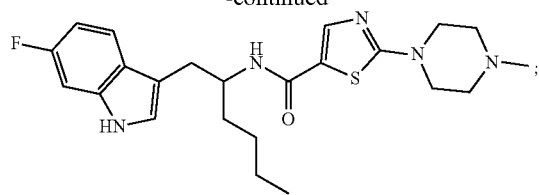

N-(1-(6-fluoro-1H-indol-3-yl)hexan-2-yl)-
2-(4-methylpiperazin-1-yl)thiazole-5-
carboxamide

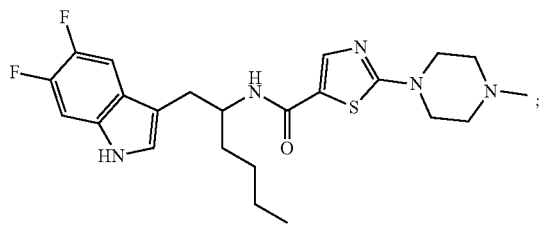

N-(1-(5,6-fluoro-1H-indol-3-yl)hexan-2-yl)-
2-(4-methylpiperazin-1-yl)thiazole-5-
carboxamide

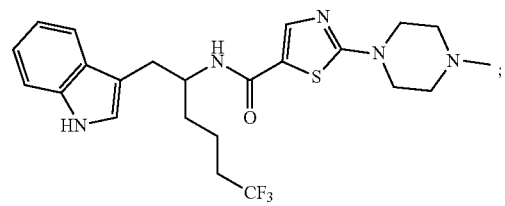

2-(4-methylpiperazin-1-yl)-N-(6,6,6-
trifluoro-1-(1H-indol-3-yl)hexan-2-
yl)thiazole-5-carboxamide

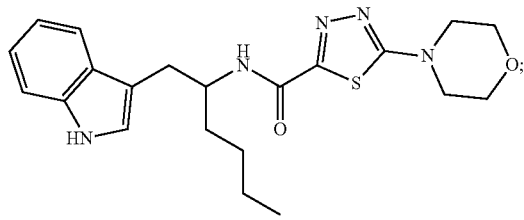

N-(1-(1H-indol-3-yl)hexan-2-yl)-5-
morpholino-1,3,4-thiadiazole-2-
carboxamide

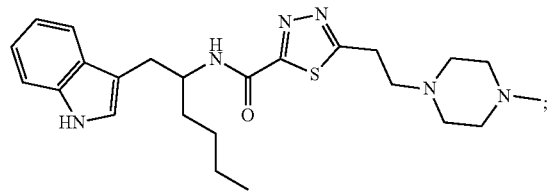

N-(1-(1H-indol-3-yl)hexan-2-yl)-5-(2-(4-
methylpiperazin-1-yl)ethyl)-1,3,4-
thiadiazole-2-carboxamide

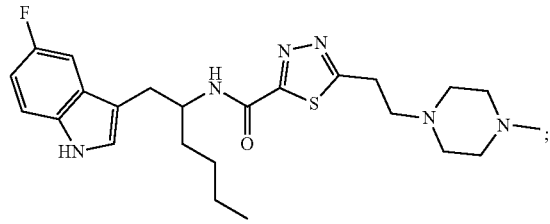

N-(1-(5-fluoro-1H-indol-3-yl)hexan-2-yl)-
5-(2-(4-methylpiperazin-1-yl)ethyl)-1,3,4-
thiadiazole-2-carboxamide -continued

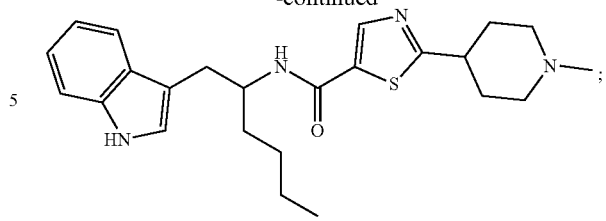

N-(1-(1H-indol-3-yl)hexan-2-yl)-2-(1-
methylpiperidin-4-yl)thiazole-5-
carboxamide

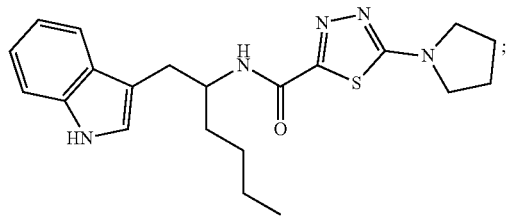

N-(1-(1H-indol-3-yl)hexan-2-yl)-5-
(pyrrolidin-1-yl)-1,3,4-thiadiazole-2-
carboxamide

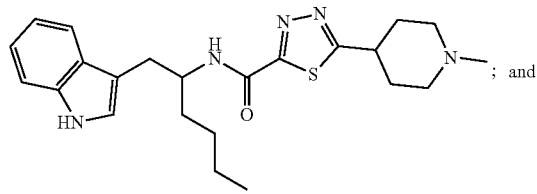

; and

N-(1-(1H-indol-3-yl)hexan-2-yl)-5-(1-
methylpiperidin-4-yl)1,3,4-thiadiazole-2-
carboxamide

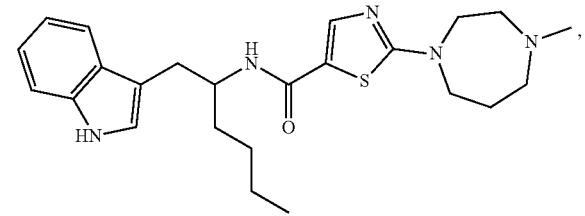

N-(1-(1H-indol-3-yl)hexan-2-yl)-2-(4-
methyl-1,4-diazepan-1-yl)thiazole-5-
carboxamide and pharmaceutically acceptable salts thereof.

31. A compound selected from the group consisting of:

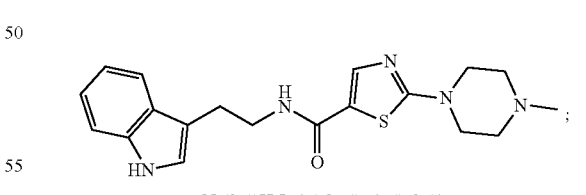

N-(2-(1H-Indol-3-yl)ethyl)-2-(4-
methylpiperazin-1-yl)thiazole-5-
carboxamide

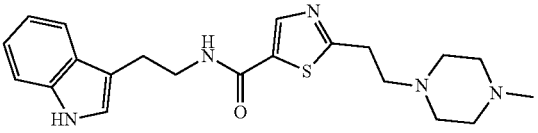

N-(2-(1H-Indol-3-yl)ethyl)-2-(2-(4-
methylpiperazin-1-yl)ethyl)thiazole-5-
carboxamide -continued

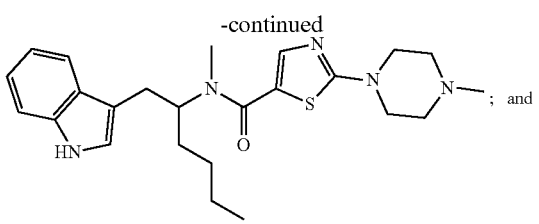

N-(1-(1H-indol-3-yl)hexan-2-yl)-N-methyl-
2-(4-methylpiperazin-1-yl)thiazole-5-
carboxamide

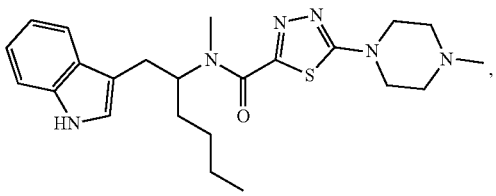

N-(1-(1H-indol-3-yl)hexan-2-yl)-N-methyl-
5-(4-methylpiperazin-1-yl)1,3,4-
thiadiazole-2-carboxamide and pharmaceutically acceptable salts thereof.

32. A pharmaceutical composition comprising (a) at least one compound or pharmaceutically acceptable salt thereof according to claim 1, and (b) a pharmaceutically acceptable excipient.

33. The pharmaceutical composition of claim 32, wherein $R^2$ is substantially in an "R" stereochemical configuration.

34. The pharmaceutical composition of claim 32, wherein $R^2$ is substantially in an "S" stereochemical configuration.

35. A method of treating a disease or medical condition associated with protein aggregation, comprising administering to a subject in need of such treatment an effective amount of at least one compound or pharmaceutically acceptable salt thereof according to claim 1, wherein the disease or medical condition associated with protein aggregation is Alzheimer's disease, Parkinson's disease, frontotemporal dementia, dementia with Lewy bodies (Lewy body disease), Parkinson's disease with dementia, multiple system atrophy, amyotrophic lateral sclerosis, Huntington's disease, or melanoma.

36. A method of interfering with the accumulation of protein or peptide aggregates in a cell, or preventing, slowing, reversing, or inhibiting protein or peptide aggregation in a cell, comprising contacting the cell with an effective amount of at least one compound or pharmaceutically acceptable salt according to claim 1, wherein the contacting is in vitro ex vivo or in vivo.

37. A method of interfering with the accumulation of protein or peptide aggregates in a cell, or preventing, slowing, reversing, or inhibiting protein or peptide aggregation in a cell, comprising contacting the cell with an effective amount of a pharmaceutical composition according to claim 32, wherein the contacting is in vitro, ex vivo, or in vivo.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Cys Thr Gly Phe Val Lys Lys Asp Gln Leu Gly Lys
1               5                   10
```